(12) United States Patent
Conlon et al.

(10) Patent No.: US 8,771,260 B2
(45) Date of Patent: Jul. 8, 2014

(54) ACTUATING AND ARTICULATING SURGICAL DEVICE

(75) Inventors: Sean P. Conlon, Loveland, OH (US); Rudolph H. Nobis, Mason, OH (US); Frederick Q. Johnson, Pleasanton, CA (US); Steven P. Woodard, Cupertino, CA (US); Ruth E. Costa, Mountain View, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1296 days.

(21) Appl. No.: 12/129,880

(22) Filed: May 30, 2008

(65) Prior Publication Data

US 2009/0299143 A1 Dec. 3, 2009

(51) Int. Cl.
| | | |
|---|---|---|
| *A61B 17/28* | (2006.01) | |
| *A61B 17/29* | (2006.01) | |
| *A61B 19/00* | (2006.01) | |
| *A61B 17/00* | (2006.01) | |

(52) U.S. Cl.
CPC .......... *A61B 17/29* (2013.01); *A61B 2019/2234* (2013.01); *A61B 2017/2927* (2013.01); *A61B 2017/00477* (2013.01)
USPC .......................................................... 606/1

(58) Field of Classification Search
CPC ........... A61B 2017/2927; A61B 17/29; A61B 19/22; A61B 2017/00477; A61B 2017/2936; A61B 2019/2234
See application file for complete search history.

(56) References Cited

U.S. PATENT DOCUMENTS

| | | |
|---|---|---|
| 645,576 A | 3/1900 | Telsa |
| 649,621 A | 5/1900 | Tesla |
| 787,412 A | 4/1905 | Tesla |
| 1,039,354 A | 9/1912 | Bonadio |
| 1,127,948 A | 2/1915 | Wappler |
| 1,482,653 A | 2/1924 | Lilly |
| 1,625,602 A | 4/1927 | Gould et al, |
| 1,916,722 A | 7/1933 | Ende |

(Continued)

FOREIGN PATENT DOCUMENTS

| | | |
|---|---|---|
| AU | 666310 B2 | 2/1996 |
| DE | 3008120 A1 | 9/1980 |

(Continued)

OTHER PUBLICATIONS

Rutala et al. "Guideline for Disinfection and Sterilization in Healthcare Facilities, 2008" (available at http://www.cdc.gov/hicpac/Disinfection_Sterilization/13_11sterilizingPractices.html).*

(Continued)

*Primary Examiner* — Gary Jackson
*Assistant Examiner* — Scott T Luan

(57) ABSTRACT

Methods and devices are provided for controlling movement of a working end of a surgical device, and in particular for performing various surgical procedures using an instrument having an end effector that can be articulated relative to an elongate shaft of the device. A decoupling member can isolate the actuation of the end effector from the articulation of the end effector. In certain embodiments, the end effector can also optionally rotate relative to the elongate shaft of the device, and/or the shaft can rotate relative to a handle of the device.

18 Claims, 22 Drawing Sheets

(56) References Cited

U.S. PATENT DOCUMENTS

| | | |
|---|---|---|
| 2,028,635 A | 1/1936 | Wappler |
| 2,031,682 A | 2/1936 | Wappler et al. |
| 2,113,246 A | 4/1938 | Wappler |
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,493,108 A | 1/1950 | Casey, Jr. |
| 2,504,152 A | 4/1950 | Riker et al. |
| 2,938,382 A | 5/1960 | De Graaf |
| 2,952,206 A | 9/1960 | Becksted |
| 3,069,195 A | 12/1962 | Buck |
| 3,070,088 A | 12/1962 | Brahos |
| 3,170,471 A | 2/1965 | Schnitzer |
| 3,435,824 A | 4/1969 | Gamponia |
| 3,470,876 A | 10/1969 | Barchilon |
| 3,595,239 A | 7/1971 | Petersen |
| 3,669,487 A | 6/1972 | Roberts et al. |
| 3,746,881 A | 7/1973 | Fitch et al. |
| 3,799,672 A | 3/1974 | Vurek |
| 3,854,473 A | 12/1974 | Matsuo |
| 3,946,740 A | 3/1976 | Bassett |
| 3,948,251 A | 4/1976 | Hosono |
| 3,961,632 A | 6/1976 | Moossun |
| 3,965,890 A | 6/1976 | Gauthier |
| 3,994,301 A | 11/1976 | Agris |
| 4,011,872 A | 3/1977 | Komiya |
| 4,012,812 A | 3/1977 | Black |
| 4,085,743 A | 4/1978 | Yoon |
| 4,164,225 A | 8/1979 | Johnson et al. |
| 4,174,715 A | 11/1979 | Hasson |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,269,174 A | 5/1981 | Adair |
| 4,278,077 A | 7/1981 | Mizumoto |
| 4,285,344 A | 8/1981 | Marshall |
| 4,311,143 A | 1/1982 | Komiya |
| 4,329,980 A | 5/1982 | Terada |
| 4,396,021 A | 8/1983 | Baumgartner |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,653,476 A | 3/1987 | Bonnet |
| 4,655,219 A | 4/1987 | Petruzzi |
| 4,669,470 A | 6/1987 | Brandfield |
| 4,671,477 A | 6/1987 | Cullen |
| 4,677,982 A | 7/1987 | Llinas et al. |
| 4,685,447 A | 8/1987 | Iversen et al. |
| 4,711,240 A | 12/1987 | Goldwasser et al. |
| 4,712,545 A | 12/1987 | Honkanen |
| 4,721,116 A | 1/1988 | Schintgen et al. |
| 4,727,600 A | 2/1988 | Avakian |
| 4,733,662 A | 3/1988 | DeSatnick et al. |
| D295,894 S | 5/1988 | Sharkany et al. |
| 4,763,669 A | 8/1988 | Jaeger |
| 4,770,188 A | 9/1988 | Chikama |
| 4,815,450 A | 3/1989 | Patel |
| 4,823,794 A | 4/1989 | Pierce |
| 4,829,999 A | 5/1989 | Auth |
| 4,867,140 A | 9/1989 | Hovis et al. |
| 4,869,238 A | 9/1989 | Opie et al. |
| 4,869,459 A * | 9/1989 | Bourne .......................... 251/58 |
| 4,873,979 A | 10/1989 | Hanna |
| 4,880,015 A * | 11/1989 | Nierman ...................... 600/564 |
| 4,911,148 A | 3/1990 | Sosnowski et al. |
| 4,926,860 A | 5/1990 | Stice et al. |
| 4,938,214 A | 7/1990 | Specht et al. |
| 4,950,273 A | 8/1990 | Briggs |
| 4,950,285 A | 8/1990 | Wilk |
| 4,953,539 A | 9/1990 | Nakamura et al. |
| 4,960,133 A | 10/1990 | Hewson |
| 4,977,887 A | 12/1990 | Gouda |
| 4,979,950 A | 12/1990 | Transue et al. |
| 4,984,581 A | 1/1991 | Stice |
| 4,994,079 A | 2/1991 | Genese et al. |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,108,421 A | 4/1992 | Fowler |
| 5,123,913 A | 6/1992 | Wilk et al. |
| 5,123,914 A | 6/1992 | Cope |
| 5,133,727 A | 7/1992 | Bales et al. |
| 5,147,374 A | 9/1992 | Fernandez |
| 5,174,300 A | 12/1992 | Bales et al. |
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,192,300 A | 3/1993 | Fowler |
| 5,197,963 A | 3/1993 | Parins |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,245,460 A | 9/1993 | Allen et al. |
| 5,246,424 A | 9/1993 | Wilk |
| 5,257,999 A | 11/1993 | Slanetz, Jr. |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,275,614 A | 1/1994 | Haber et al. |
| 5,275,616 A | 1/1994 | Fowler |
| 5,284,128 A | 2/1994 | Hart |
| 5,284,162 A | 2/1994 | Wilk |
| 5,287,845 A | 2/1994 | Faul et al. |
| 5,287,852 A | 2/1994 | Arkinstall |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,297,687 A | 3/1994 | Freed |
| 5,301,061 A | 4/1994 | Nakada et al. |
| 5,312,023 A | 5/1994 | Green et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,318,589 A | 6/1994 | Lichtman |
| 5,320,636 A | 6/1994 | Slater |
| 5,324,261 A | 6/1994 | Amundson et al. |
| 5,325,845 A | 7/1994 | Adair |
| 5,330,471 A | 7/1994 | Eggers |

(56) References Cited

U.S. PATENT DOCUMENTS

| | | | |
|---|---|---|---|
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,168 A | 8/1994 | Hemmer |
| 5,334,198 A | 8/1994 | Hart et al. |
| 5,341,815 A | 8/1994 | Cofone et al. |
| 5,342,396 A | 8/1994 | Cook |
| 5,344,428 A | 9/1994 | Griffiths |
| 5,345,927 A | 9/1994 | Bonutti |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,381 A | 10/1994 | Ensminger et al. |
| 5,356,408 A | 10/1994 | Rydell |
| 5,360,428 A | 11/1994 | Hutchinson, Jr. |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A * | 12/1994 | Hassler .................. 606/207 |
| 5,377,695 A | 1/1995 | An Haack |
| 5,383,877 A | 1/1995 | Clarke |
| 5,383,888 A | 1/1995 | Zvenyatsky et al. |
| 5,386,817 A | 2/1995 | Jones |
| 5,387,259 A | 2/1995 | Davidson |
| 5,391,174 A | 2/1995 | Weston |
| 5,392,789 A | 2/1995 | Slater et al. |
| 5,395,386 A | 3/1995 | Slater |
| 5,401,248 A | 3/1995 | Bencini |
| 5,403,311 A | 4/1995 | Abele et al. |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,433,721 A | 7/1995 | Hooven et al. |
| 5,439,471 A | 8/1995 | Kerr |
| 5,439,478 A | 8/1995 | Palmer |
| 5,441,059 A | 8/1995 | Dannan |
| 5,441,494 A | 8/1995 | Ortiz |
| 5,441,499 A | 8/1995 | Fritzsch |
| 5,443,463 A | 8/1995 | Stern et al. |
| 5,445,638 A | 8/1995 | Rydell et al. |
| 5,445,648 A | 8/1995 | Cook |
| 5,449,021 A | 9/1995 | Chikama |
| 5,454,827 A | 10/1995 | Aust et al. |
| 5,456,667 A | 10/1995 | Ham et al. |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,478,347 A | 12/1995 | Aranyi |
| 5,478,352 A | 12/1995 | Fowler |
| 5,480,404 A | 1/1996 | Kammerer et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schülken et al. |
| 5,499,992 A | 3/1996 | Meade et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,518,501 A | 5/1996 | Oneda et al. |
| 5,522,829 A | 6/1996 | Michalos |
| 5,522,830 A | 6/1996 | Aranyi |
| 5,527,321 A | 6/1996 | Hinchliffe |
| 5,533,418 A | 7/1996 | Wu et al. |
| 5,536,248 A | 7/1996 | Weaver et al. |
| 5,538,509 A | 7/1996 | Dunlap et al. |
| 5,540,648 A | 7/1996 | Yoon |
| 5,549,637 A | 8/1996 | Crainich |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,571,090 A | 11/1996 | Sherts |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,591,179 A | 1/1997 | Edelstein |
| 5,591,205 A | 1/1997 | Fowler |
| 5,593,420 A | 1/1997 | Eubanks, Jr et al. |
| 5,595,562 A | 1/1997 | Grier |
| 5,597,378 A | 1/1997 | Jervis |
| 5,601,573 A | 2/1997 | Fogelberg et al. |
| 5,601,588 A | 2/1997 | Tonomura et al. |
| 5,601,602 A | 2/1997 | Fowler |
| 5,604,531 A | 2/1997 | Iddan et al. |
| 5,607,389 A | 3/1997 | Edwards et al. |
| 5,607,406 A | 3/1997 | Hernandez et al. |
| 5,607,450 A | 3/1997 | Zvenyatsky et al. |
| 5,609,601 A | 3/1997 | Kolesa et al. |
| 5,613,975 A | 3/1997 | Christy |
| 5,616,117 A | 4/1997 | Dinkler et al. |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,626,578 A | 5/1997 | Tihon |
| 5,626,587 A * | 5/1997 | Bishop et al. ............... 606/143 |
| 5,628,732 A | 5/1997 | Antoon, Jr. et al. |
| 5,630,782 A | 5/1997 | Adair |
| 5,643,283 A | 7/1997 | Younker |
| 5,643,292 A | 7/1997 | Hart |
| 5,643,294 A | 7/1997 | Tovey et al. |
| 5,644,798 A | 7/1997 | Shah |
| 5,645,083 A | 7/1997 | Essig et al. |
| 5,645,565 A | 7/1997 | Rudd et al. |
| 5,649,372 A | 7/1997 | Souza |
| 5,653,677 A | 8/1997 | Okada et al. |
| 5,653,690 A | 8/1997 | Booth et al. |
| 5,653,722 A | 8/1997 | Kieturakis |
| 5,657,755 A | 8/1997 | Desai |
| 5,662,621 A | 9/1997 | Lafontaine |
| 5,662,663 A | 9/1997 | Shallman |
| 5,667,527 A | 9/1997 | Cook |
| 5,669,875 A | 9/1997 | van Eerdenburg |
| 5,681,324 A | 10/1997 | Kammerer et al. |
| 5,681,330 A | 10/1997 | Hughett et al. |
| 5,685,820 A | 11/1997 | Riek et al. |
| 5,690,606 A | 11/1997 | Slotman |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |

(56) References Cited

U.S. PATENT DOCUMENTS

| | | |
|---|---|---|
| 5,702,438 A | 12/1997 | Avitall |
| 5,704,892 A | 1/1998 | Adair |
| 5,709,708 A | 1/1998 | Thal |
| 5,711,921 A | 1/1998 | Langford |
| 5,716,326 A | 2/1998 | Dannan |
| 5,716,375 A | 2/1998 | Fowler |
| 5,728,094 A | 3/1998 | Edwards |
| 5,730,740 A | 3/1998 | Wales et al. |
| 5,735,849 A | 4/1998 | Baden et al. |
| 5,741,234 A | 4/1998 | Aboul-Hosn |
| 5,741,278 A | 4/1998 | Stevens |
| 5,741,285 A | 4/1998 | McBrayer et al. |
| 5,741,429 A | 4/1998 | Donadio, III et al. |
| 5,743,456 A | 4/1998 | Jones et al. |
| 5,746,759 A | 5/1998 | Meade et al. |
| 5,749,826 A | 5/1998 | Faulkner |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,762,604 A | 6/1998 | Kieturakis |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,779,701 A | 7/1998 | McBrayer et al. |
| 5,779,716 A | 7/1998 | Cano et al. |
| 5,779,727 A | 7/1998 | Orejola |
| 5,782,859 A | 7/1998 | Nicholas et al. |
| 5,782,861 A | 7/1998 | Cragg et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,797,959 A | 8/1998 | Castro et al. |
| 5,803,903 A | 9/1998 | Athas et al. |
| 5,808,665 A | 9/1998 | Green |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,058 A | 9/1998 | Carlson et al. |
| 5,817,061 A | 10/1998 | Goodwin et al. |
| 5,817,107 A | 10/1998 | Schaller |
| 5,817,119 A | 10/1998 | Klieman et al. |
| 5,819,736 A | 10/1998 | Avny et al. |
| 5,823,947 A | 10/1998 | Yoon et al. |
| 5,824,071 A | 10/1998 | Nelson et al. |
| 5,827,276 A | 10/1998 | LeVeen et al. |
| 5,827,281 A | 10/1998 | Levin |
| 5,827,299 A | 10/1998 | Thomason et al. |
| 5,827,323 A | 10/1998 | Klieman et al. |
| 5,830,231 A | 11/1998 | Geiges, Jr. |
| 5,833,603 A | 11/1998 | Kovacs et al. |
| 5,833,700 A | 11/1998 | Fogelberg et al. |
| 5,833,703 A | 11/1998 | Manushakian |
| 5,836,960 A | 11/1998 | Kolesa et al. |
| 5,843,017 A | 12/1998 | Yoon |
| 5,843,121 A | 12/1998 | Yoon |
| 5,849,022 A | 12/1998 | Sakashita et al. |
| 5,853,374 A | 12/1998 | Hart et al. |
| 5,855,585 A | 1/1999 | Kontos |
| 5,860,913 A | 1/1999 | Yamaya et al. |
| 5,860,995 A | 1/1999 | Berkelaar |
| 5,868,762 A | 2/1999 | Cragg et al. |
| 5,876,411 A | 3/1999 | Kontos |
| 5,882,331 A | 3/1999 | Sasaki |
| 5,882,344 A | 3/1999 | Stouder, Jr. |
| 5,893,846 A | 4/1999 | Bales et al. |
| 5,893,874 A | 4/1999 | Bourque et al. |
| 5,893,875 A | 4/1999 | O'Connor et al. |
| 5,897,487 A | 4/1999 | Ouchi |
| 5,899,919 A | 5/1999 | Eubanks, Jr. et al. |
| 5,902,254 A | 5/1999 | Magram |
| 5,904,702 A | 5/1999 | Ek et al. |
| 5,908,420 A | 6/1999 | Parins et al. |
| 5,908,429 A | 6/1999 | Yoon |
| 5,911,737 A | 6/1999 | Lee et al. |
| 5,916,146 A | 6/1999 | Allotta et al. |
| 5,916,147 A | 6/1999 | Boury |
| 5,921,993 A | 7/1999 | Yoon |
| 5,921,997 A | 7/1999 | Fogelberg et al. |
| 5,922,008 A | 7/1999 | Gimpelson |
| 5,925,052 A | 7/1999 | Simmons |
| 5,928,255 A | 7/1999 | Meade et al. |
| 5,928,266 A | 7/1999 | Kontos |
| 5,936,536 A | 8/1999 | Morris |
| 5,944,718 A | 8/1999 | Austin et al. |
| 5,951,547 A | 9/1999 | Gough et al. |
| 5,951,549 A | 9/1999 | Richardson et al. |
| 5,954,720 A | 9/1999 | Wilson et al. |
| 5,954,731 A | 9/1999 | Yoon |
| 5,957,936 A | 9/1999 | Yoon et al. |
| 5,957,943 A | 9/1999 | Vaitekunas |
| 5,957,953 A | 9/1999 | DiPoto et al. |
| 5,964,782 A | 10/1999 | Lafontaine et al. |
| 5,971,995 A | 10/1999 | Rousseau |
| 5,972,002 A | 10/1999 | Bark et al. |
| 5,976,074 A | 11/1999 | Moriyama |
| 5,976,075 A | 11/1999 | Beane et al. |
| 5,976,130 A | 11/1999 | McBrayer et al. |
| 5,976,131 A | 11/1999 | Guglielmi et al. |
| 5,980,539 A | 11/1999 | Kontos |
| 5,980,556 A | 11/1999 | Giordano et al. |
| 5,984,938 A | 11/1999 | Yoon |
| 5,984,939 A | 11/1999 | Yoon |
| 5,984,950 A | 11/1999 | Cragg et al. |
| 5,989,182 A | 11/1999 | Hori et al. |
| 5,993,447 A | 11/1999 | Blewett et al. |
| 5,993,474 A | 11/1999 | Ouchi |
| 5,995,875 A | 11/1999 | Blewett et al. |
| 5,997,555 A | 12/1999 | Kontos |
| 6,001,120 A | 12/1999 | Levin |
| 6,004,269 A | 12/1999 | Crowley et al. |
| 6,004,330 A | 12/1999 | Middleman et al. |
| 6,007,566 A | 12/1999 | Wenstrom, Jr. |
| 6,010,515 A | 1/2000 | Swain et al. |
| 6,012,494 A | 1/2000 | Balazs |
| 6,016,452 A | 1/2000 | Kasevich |
| 6,017,356 A | 1/2000 | Frederick et al. |
| 6,019,770 A | 2/2000 | Christoudias |
| 6,024,708 A | 2/2000 | Bales et al. |
| 6,024,747 A | 2/2000 | Kontos |
| 6,027,522 A | 2/2000 | Palmer |
| 6,030,365 A | 2/2000 | Laufer |
| 6,030,384 A | 2/2000 | Nezhat |
| 6,030,634 A | 2/2000 | Wu et al. |
| 6,033,399 A | 3/2000 | Gines |
| 6,036,685 A | 3/2000 | Mueller |
| 6,053,927 A | 4/2000 | Hamas |
| 6,053,937 A | 4/2000 | Edwards et al. |
| 6,066,160 A | 5/2000 | Colvin et al. |
| 6,068,603 A | 5/2000 | Suzuki |
| 6,068,629 A | 5/2000 | Haissaguerre et al. |
| 6,071,233 A | 6/2000 | Ishikawa et al. |
| 6,074,408 A | 6/2000 | Freeman |
| 6,086,530 A | 7/2000 | Mack |
| 6,090,105 A | 7/2000 | Zepeda et al. |
| 6,090,108 A | 7/2000 | McBrayer et al. |
| 6,090,129 A | 7/2000 | Ouchi |
| 6,096,046 A | 8/2000 | Weiss |
| 6,102,909 A | 8/2000 | Chen et al. |
| 6,102,926 A | 8/2000 | Tartaglia et al. |
| 6,106,473 A | 8/2000 | Violante et al. |
| 6,106,521 A | 8/2000 | Blewett et al. |
| 6,109,852 A | 8/2000 | Shahinpoor et al. |
| 6,110,154 A | 8/2000 | Shimomura et al. |

(56) References Cited

U.S. PATENT DOCUMENTS

| | | |
|---|---|---|
| 6,110,183 A | 8/2000 | Cope |
| 6,113,593 A | 9/2000 | Tu et al. |
| 6,117,144 A | 9/2000 | Nobles et al. |
| 6,117,158 A | 9/2000 | Measamer et al. |
| 6,139,555 A | 10/2000 | Hart et al. |
| 6,141,037 A | 10/2000 | Upton et al. |
| 6,146,391 A | 11/2000 | Cigaina |
| 6,148,222 A | 11/2000 | Ramsey, III |
| 6,149,653 A | 11/2000 | Deslauriers |
| 6,149,662 A | 11/2000 | Pugliesi et al. |
| 6,152,920 A | 11/2000 | Thompson et al. |
| 6,156,006 A | 12/2000 | Brosens et al. |
| 6,159,200 A | 12/2000 | Verdura et al. |
| 6,165,175 A | 12/2000 | Wampler et al. |
| 6,165,184 A | 12/2000 | Verdura et al. |
| 6,168,570 B1 | 1/2001 | Ferrera |
| 6,168,605 B1 | 1/2001 | Measamer et al. |
| 6,169,269 B1 | 1/2001 | Maynard |
| 6,170,130 B1 | 1/2001 | Hamilton et al. |
| 6,179,776 B1 | 1/2001 | Adams et al. |
| 6,179,832 B1 | 1/2001 | Jones et al. |
| 6,179,837 B1 | 1/2001 | Hooven |
| 6,183,420 B1 | 2/2001 | Douk et al. |
| 6,190,353 B1 | 2/2001 | Makower et al. |
| 6,190,383 B1 | 2/2001 | Schmaltz et al. |
| 6,190,384 B1 | 2/2001 | Ouchi |
| 6,190,399 B1 | 2/2001 | Palmer et al. |
| 6,203,533 B1 | 3/2001 | Ouchi |
| 6,206,872 B1 | 3/2001 | Lafond et al. |
| 6,206,877 B1 | 3/2001 | Kese et al. |
| 6,206,904 B1 | 3/2001 | Ouchi |
| 6,210,409 B1 | 4/2001 | Ellman et al. |
| 6,214,007 B1 | 4/2001 | Anderson |
| 6,214,028 B1 | 4/2001 | Yoon et al. |
| 6,216,043 B1 | 4/2001 | Swanson et al. |
| 6,228,096 B1 | 5/2001 | Marchand |
| 6,231,506 B1 | 5/2001 | Hu et al. |
| 6,234,958 B1 | 5/2001 | Snoke et al. |
| 6,245,079 B1 | 6/2001 | Nobles et al. |
| 6,246,914 B1 | 6/2001 | de la Rama et al. |
| 6,258,064 B1 | 7/2001 | Smith et al. |
| 6,261,242 B1 | 7/2001 | Roberts et al. |
| 6,264,664 B1 | 7/2001 | Avellanet |
| 6,270,497 B1 | 8/2001 | Sekino et al. |
| 6,270,505 B1 | 8/2001 | Yoshida et al. |
| 6,277,136 B1 | 8/2001 | Bonutti |
| 6,283,963 B1 | 9/2001 | Regula |
| 6,293,909 B1 | 9/2001 | Chu et al. |
| 6,293,952 B1 | 9/2001 | Brosens et al. |
| 6,296,630 B1 | 10/2001 | Altman et al. |
| 6,314,963 B1 | 11/2001 | Vaska et al. |
| 6,322,578 B1 | 11/2001 | Houle et al. |
| 6,325,534 B1 | 12/2001 | Hawley et al. |
| 6,326,177 B1 | 12/2001 | Schoenbach et al. |
| 6,328,730 B1 | 12/2001 | Harkrider, Jr. |
| 6,350,267 B1 | 2/2002 | Stefanchik |
| 6,350,278 B1 | 2/2002 | Lenker et al. |
| 6,352,503 B1 | 3/2002 | Matsui et al. |
| 6,352,543 B1 | 3/2002 | Cole |
| 6,355,013 B1 | 3/2002 | van Muiden |
| 6,355,035 B1 | 3/2002 | Manushakian |
| 6,361,534 B1 | 3/2002 | Chen et al. |
| 6,364,879 B1 | 4/2002 | Chen et al. |
| 6,368,340 B2 | 4/2002 | Malecki et al. |
| 6,371,956 B1 | 4/2002 | Wilson et al. |
| 6,379,366 B1 | 4/2002 | Fleischman et al. |
| 6,383,195 B1 | 5/2002 | Richard |
| 6,383,197 B1 | 5/2002 | Conlon et al. |
| 6,387,671 B1 | 5/2002 | Rubinsky et al. |
| 6,391,029 B1 | 5/2002 | Hooven et al. |
| 6,398,708 B1 | 6/2002 | Hastings et al. |
| 6,402,735 B1 | 6/2002 | Langevin |
| 6,402,746 B1 | 6/2002 | Whayne et al. |
| 6,406,440 B1 | 6/2002 | Stefanchik |
| 6,409,727 B1 | 6/2002 | Bales et al. |
| 6,409,733 B1 | 6/2002 | Conlon et al. |
| 6,419,639 B2 | 7/2002 | Walther et al. |
| 6,419,641 B1 | 7/2002 | Mark et al. |
| 6,427,089 B1 | 7/2002 | Knowlton |
| 6,431,500 B1 | 8/2002 | Jacobs et al. |
| 6,436,107 B1 | 8/2002 | Wang et al. |
| 6,443,970 B1 | 9/2002 | Schulze et al. |
| 6,443,988 B2 | 9/2002 | Felt et al. |
| 6,447,511 B1 | 9/2002 | Slater |
| 6,447,523 B1 | 9/2002 | Middleman et al. |
| 6,454,783 B1 | 9/2002 | Piskun |
| 6,454,785 B2 | 9/2002 | De Hoyos Garza |
| 6,458,076 B1 | 10/2002 | Pruitt |
| 6,464,701 B1 | 10/2002 | Hooven et al. |
| 6,464,702 B2 | 10/2002 | Schulze et al. |
| 6,470,218 B1 | 10/2002 | Behl |
| 6,475,104 B1 | 11/2002 | Lutz et al. |
| 6,485,411 B1 | 11/2002 | Konstorum et al. |
| 6,489,745 B1 | 12/2002 | Koreis |
| 6,491,626 B1 | 12/2002 | Stone et al. |
| 6,491,627 B1 | 12/2002 | Komi |
| 6,491,691 B1 | 12/2002 | Morley et al. |
| 6,493,590 B1 | 12/2002 | Wessman et al. |
| 6,494,893 B2 | 12/2002 | Dubrul et al. |
| 6,500,176 B1 | 12/2002 | Truckai et al. |
| 6,503,192 B1 | 1/2003 | Ouchi |
| 6,506,190 B1 | 1/2003 | Walshe |
| 6,508,827 B1 | 1/2003 | Manhes |
| 6,514,239 B2 | 2/2003 | Shimmura et al. |
| 6,520,954 B2 | 2/2003 | Ouchi |
| 6,526,320 B2 | 2/2003 | Mitchell |
| 6,527,782 B2 | 3/2003 | Hogg et al. |
| 6,530,922 B2 | 3/2003 | Cosman et al. |
| 6,535,764 B2 | 3/2003 | Imran et al. |
| 6,537,200 B2 | 3/2003 | Leysieffer et al. |
| 6,543,456 B1 | 4/2003 | Freeman |
| 6,551,270 B1 | 4/2003 | Bimbo et al. |
| 6,554,766 B2 | 4/2003 | Maeda et al. |
| 6,554,823 B2 | 4/2003 | Palmer et al. |
| 6,554,829 B2 | 4/2003 | Schulze et al. |
| 6,558,384 B2 | 5/2003 | Mayenberger |
| 6,562,034 B2 | 5/2003 | Edwards et al. |
| 6,562,035 B1 | 5/2003 | Levin |
| 6,562,052 B2 | 5/2003 | Nobles et al. |
| 6,569,159 B1 | 5/2003 | Edwards et al. |
| 6,572,629 B2 | 6/2003 | Kalloo et al. |
| 6,572,635 B1 | 6/2003 | Bonutti |
| 6,575,988 B2 | 6/2003 | Rousseau |
| 6,579,311 B1 | 6/2003 | Makower |
| 6,581,889 B2 | 6/2003 | Carpenter et al. |
| 6,585,642 B2 | 7/2003 | Christopher |
| 6,585,717 B1 | 7/2003 | Wittenberger et al. |
| 6,587,750 B2 | 7/2003 | Gerbi et al. |
| 6,592,559 B1 | 7/2003 | Pakter et al. |
| 6,592,603 B2 | 7/2003 | Lasner |
| 6,602,262 B2 | 8/2003 | Griego et al. |
| 6,605,105 B1 | 8/2003 | Cuschieri et al. |
| 6,610,072 B1 | 8/2003 | Christy et al. |
| 6,610,074 B2 | 8/2003 | Santilli |
| 6,613,038 B2 | 9/2003 | Bonutti et al. |
| 6,613,068 B2 | 9/2003 | Ouchi |
| 6,616,632 B2 | 9/2003 | Sharp et al. |
| 6,620,193 B1 | 9/2003 | Lau et al. |
| 6,623,448 B2 | 9/2003 | Slater |
| 6,626,919 B1 | 9/2003 | Swanstrom |
| 6,632,229 B1 | 10/2003 | Yamanouchi |
| 6,632,234 B1 | 10/2003 | Kieturakis et al. |
| 6,638,275 B1 | 10/2003 | McGaffigan et al. |
| 6,638,286 B1 | 10/2003 | Burbank et al. |
| 6,645,225 B1 | 11/2003 | Atkinson |
| 6,652,518 B2 | 11/2003 | Wellman et al. |
| 6,652,521 B1 | 11/2003 | Schulze |
| 6,652,551 B1 | 11/2003 | Heiss |
| 6,656,194 B1 | 12/2003 | Gannoe et al. |
| 6,663,641 B1 | 12/2003 | Kovac et al. |
| 6,663,655 B2 | 12/2003 | Ginn et al. |
| 6,666,854 B1 | 12/2003 | Lange |
| 6,672,338 B1 | 1/2004 | Esashi et al. |
| 6,673,058 B2 | 1/2004 | Snow |

(56) References Cited

U.S. PATENT DOCUMENTS

| | | |
|---|---|---|
| 6,673,087 B1 | 1/2004 | Chang et al. |
| 6,673,092 B1 | 1/2004 | Bacher |
| 6,679,882 B1 | 1/2004 | Kornerup |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,692,493 B2 | 2/2004 | McGovern et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,188 B2 | 3/2004 | Ushimaru |
| 6,709,445 B2 | 3/2004 | Boebel et al. |
| 6,716,226 B2 | 4/2004 | Sixto, Jr. et al. |
| 6,731,875 B1 | 5/2004 | Kartalopoulos |
| 6,736,822 B2 | 5/2004 | McClellan et al. |
| 6,740,030 B2 | 5/2004 | Martone et al. |
| 6,743,166 B2 | 6/2004 | Berci et al. |
| 6,743,226 B2 | 6/2004 | Cosman et al. |
| 6,743,239 B1 | 6/2004 | Kuehn et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,758,857 B2 | 7/2004 | Cioanta et al. |
| 6,761,685 B2 | 7/2004 | Adams et al. |
| 6,761,718 B2 | 7/2004 | Madsen |
| 6,761,722 B2 | 7/2004 | Cole et al. |
| 6,773,434 B2 | 8/2004 | Ciarrocca |
| 6,776,787 B2 | 8/2004 | Phung et al. |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,382 B1 | 9/2004 | Hoffman |
| 6,786,864 B2 | 9/2004 | Matsuura et al. |
| 6,786,905 B2 | 9/2004 | Swanson et al. |
| 6,788,977 B2 | 9/2004 | Fenn et al. |
| 6,790,173 B2 | 9/2004 | Saadat et al. |
| 6,790,217 B2 | 9/2004 | Schulze et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,817,974 B2 | 11/2004 | Cooper et al. |
| 6,818,007 B1 | 11/2004 | Dampney et al. |
| 6,824,548 B2 | 11/2004 | Smith et al. |
| 6,830,545 B2 | 12/2004 | Bendall |
| 6,836,688 B2 | 12/2004 | Ingle et al. |
| 6,837,847 B2 | 1/2005 | Ewers et al. |
| 6,840,246 B2 | 1/2005 | Downing |
| 6,840,938 B1 | 1/2005 | Morley et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,866,628 B2 | 3/2005 | Goodman et al. |
| 6,869,394 B2 | 3/2005 | Ishibiki |
| 6,878,106 B1 | 4/2005 | Herrmann |
| 6,878,110 B2 | 4/2005 | Yang et al. |
| 6,881,213 B2 | 4/2005 | Ryan et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,896,683 B1 | 5/2005 | Gadberry et al. |
| 6,896,692 B2 | 5/2005 | Ginn et al. |
| 6,899,710 B2 | 5/2005 | Hooven |
| 6,908,427 B2 | 6/2005 | Fleener et al. |
| 6,908,476 B2 | 6/2005 | Jud et al. |
| 6,913,613 B2 | 7/2005 | Schwarz et al. |
| 6,916,284 B2 | 7/2005 | Moriyama |
| 6,918,871 B2 | 7/2005 | Schulze |
| 6,918,908 B2 | 7/2005 | Bonner et al. |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,932,834 B2 | 8/2005 | Lizardi et al. |
| 6,936,003 B2 | 8/2005 | Iddan |
| 6,939,327 B2 | 9/2005 | Hall et al. |
| 6,942,613 B2 | 9/2005 | Ewers et al. |
| 6,944,490 B1 | 9/2005 | Chow |
| 6,945,472 B2 | 9/2005 | Wuttke et al. |
| 6,945,979 B2 | 9/2005 | Kortenbach et al. |
| 6,955,683 B2 | 10/2005 | Bonutti |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,991,631 B2 | 1/2006 | Woloszko et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,001,341 B2 | 2/2006 | Gellman et al. |
| 7,008,375 B2 | 3/2006 | Weisel |
| 7,008,419 B2 | 3/2006 | Shadduck |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,029,450 B2 | 4/2006 | Gellman |
| 7,032,600 B2 | 4/2006 | Fukuda et al. |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,071 B2 * | 8/2006 | Nicholas et al. ............... 606/206 |
| 7,088,923 B2 | 8/2006 | Haruyama |
| 7,090,673 B2 | 8/2006 | Dycus et al. |
| 7,090,683 B2 | 8/2006 | Brock et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,696 B2 | 9/2006 | Daniel et al. |
| 7,108,703 B2 | 9/2006 | Danitz et al. |
| 7,112,208 B2 | 9/2006 | Morris et al. |
| 7,115,092 B2 | 10/2006 | Park et al. |
| 7,115,124 B1 | 10/2006 | Xiao |
| 7,117,703 B2 | 10/2006 | Kato et al. |
| 7,118,531 B2 | 10/2006 | Krill |

(56) References Cited

U.S. PATENT DOCUMENTS

| | | | |
|---|---|---|---|
| 7,118,578 | B2 | 10/2006 | West, Jr. et al. |
| 7,118,587 | B2 | 10/2006 | Dycus et al. |
| 7,128,708 | B2 | 10/2006 | Saadat et al. |
| 7,130,697 | B2 | 10/2006 | Chornenky et al. |
| RE39,415 | E | 11/2006 | Bales et al. |
| 7,131,978 | B2 | 11/2006 | Sancoff et al. |
| 7,131,979 | B2 | 11/2006 | DiCarlo et al. |
| 7,131,980 | B1 | 11/2006 | Field et al. |
| 7,137,980 | B2 | 11/2006 | Buysse et al. |
| 7,137,981 | B2 | 11/2006 | Long |
| 7,146,984 | B2 | 12/2006 | Stack et al. |
| 7,147,650 | B2 | 12/2006 | Lee |
| 7,150,097 | B2 | 12/2006 | Sremcich et al. |
| 7,150,655 | B2 | 12/2006 | Mastrototaro et al. |
| 7,150,750 | B2 | 12/2006 | Damarati |
| 7,152,488 | B2 | 12/2006 | Hedrich et al. |
| 7,153,321 | B2 | 12/2006 | Andrews |
| 7,160,296 | B2 | 1/2007 | Pearson et al. |
| 7,163,525 | B2 | 1/2007 | Franer |
| 7,172,714 | B2 | 2/2007 | Jacobson |
| 7,179,254 | B2 | 2/2007 | Pendekanti et al. |
| 7,188,627 | B2 | 3/2007 | Nelson et al. |
| 7,195,612 | B2 | 3/2007 | Van Sloten et al. |
| 7,195,631 | B2 | 3/2007 | Dumbauld |
| 7,204,820 | B2 | 4/2007 | Akahoshi |
| 7,208,005 | B2 | 4/2007 | Frecker et al. |
| 7,211,092 | B2 | 5/2007 | Hughett |
| 7,220,227 | B2 | 5/2007 | Sasaki et al. |
| 7,223,272 | B2 | 5/2007 | Francese et al. |
| 7,229,438 | B2 | 6/2007 | Young |
| 7,232,414 | B2 | 6/2007 | Gonzalez |
| 7,232,445 | B2 | 6/2007 | Kortenbach et al. |
| 7,235,089 | B1 | 6/2007 | McGuckin, Jr. |
| 7,241,290 | B2 | 7/2007 | Doyle et al. |
| 7,244,228 | B2 | 7/2007 | Lubowski |
| 7,250,027 | B2 | 7/2007 | Barry |
| 7,252,660 | B2 | 8/2007 | Kunz |
| 7,255,675 | B2 | 8/2007 | Gertner et al. |
| 7,261,725 | B2 | 8/2007 | Binmoeller |
| 7,270,663 | B2 | 9/2007 | Nakao |
| 7,291,127 | B2 | 11/2007 | Eidenschink |
| 7,294,139 | B1 | 11/2007 | Gengler |
| 7,301,250 | B2 | 11/2007 | Cassel |
| 7,306,597 | B2 | 12/2007 | Manzo |
| 7,308,828 | B2 | 12/2007 | Hashimoto |
| 7,318,802 | B2 | 1/2008 | Suzuki et al. |
| 7,320,695 | B2 | 1/2008 | Carroll |
| 7,322,934 | B2 | 1/2008 | Miyake et al. |
| 7,323,006 | B2 | 1/2008 | Andreas et al. |
| 7,329,256 | B2 | 2/2008 | Johnson et al. |
| 7,329,257 | B2 | 2/2008 | Kanehira et al. |
| 7,329,383 | B2 | 2/2008 | Stinson |
| 7,335,220 | B2 | 2/2008 | Khosravi et al. |
| 7,344,536 | B1 | 3/2008 | Lunsford et al. |
| 7,352,387 | B2 | 4/2008 | Yamamoto |
| 7,364,582 | B2 | 4/2008 | Lee |
| 7,371,215 | B2 | 5/2008 | Colliou et al. |
| 7,381,216 | B2 | 6/2008 | Buzzard et al. |
| 7,390,324 | B2 | 6/2008 | Whalen et al. |
| 7,393,322 | B2 | 7/2008 | Wenchell |
| 7,402,162 | B2 | 7/2008 | Ouchi |
| 7,404,791 | B2 | 7/2008 | Linares et al. |
| 7,410,483 | B2 | 8/2008 | Danitz et al. |
| 7,413,563 | B2 | 8/2008 | Corcoran et al. |
| 7,416,554 | B2 | 8/2008 | Lam et al. |
| 7,422,590 | B2 | 9/2008 | Kupferschmid et al. |
| 7,435,229 | B2 | 10/2008 | Wolf |
| 7,435,257 | B2 | 10/2008 | Lashinski et al. |
| 7,452,327 | B2 | 11/2008 | Durgin et al. |
| 7,455,208 | B2 | 11/2008 | Wales et al. |
| 7,468,066 | B2 | 12/2008 | Vargas et al. |
| 7,476,237 | B2 | 1/2009 | Taniguchi et al. |
| 7,485,093 | B2 | 2/2009 | Glukhovsky |
| 7,488,295 | B2 | 2/2009 | Burbank et al. |
| 7,494,499 | B2 | 2/2009 | Nagase et al. |
| 7,497,867 | B2 | 3/2009 | Lasner et al. |
| 7,498,950 | B1 | 3/2009 | Ertas et al. |
| 7,507,200 | B2 | 3/2009 | Okada |
| 7,510,107 | B2 | 3/2009 | Timm et al. |
| 7,511,733 | B2 | 3/2009 | Takizawa et al. |
| 7,515,953 | B2 | 4/2009 | Madar et al. |
| 7,520,876 | B2 | 4/2009 | Ressemann et al. |
| 7,524,281 | B2 | 4/2009 | Chu et al. |
| 7,524,302 | B2 | 4/2009 | Tower |
| 7,534,228 | B2 | 5/2009 | Williams |
| 7,540,872 | B2 | 6/2009 | Schechter et al. |
| 7,542,807 | B2 | 6/2009 | Bertolero et al. |
| 7,544,203 | B2 | 6/2009 | Chin et al. |
| 7,548,040 | B2 | 6/2009 | Lee et al. |
| 7,549,564 | B2 | 6/2009 | Boudreaux |
| 7,549,998 | B2 | 6/2009 | Braun |
| 7,553,278 | B2 | 6/2009 | Kucklick |
| 7,553,298 | B2 | 6/2009 | Hunt et al. |
| 7,559,452 | B2 | 7/2009 | Wales et al. |
| 7,559,887 | B2 | 7/2009 | Dannan |
| 7,559,916 | B2 | 7/2009 | Smith et al. |
| 7,560,006 | B2 | 7/2009 | Rakos et al. |
| 7,561,907 | B2 | 7/2009 | Fuimaono et al. |
| 7,561,916 | B2 | 7/2009 | Hunt et al. |
| 7,566,334 | B2 | 7/2009 | Christian et al. |
| 7,575,144 | B2 | 8/2009 | Ortiz et al. |
| 7,575,548 | B2 | 8/2009 | Takemoto et al. |
| 7,579,550 | B2 | 8/2009 | Dayton et al. |
| 7,582,096 | B2 | 9/2009 | Gellman et al. |
| 7,588,177 | B2 | 9/2009 | Racenet |
| 7,588,557 | B2 | 9/2009 | Nakao |
| 7,597,229 | B2 | 10/2009 | Boudreaux et al. |
| 7,604,150 | B2 | 10/2009 | Boudreaux |
| 7,611,479 | B2 | 11/2009 | Cragg et al. |
| 7,618,398 | B2 | 11/2009 | Holman et al. |
| 7,621,936 | B2 | 11/2009 | Cragg et al. |
| 7,632,250 | B2 | 12/2009 | Smith et al. |
| 7,635,373 | B2 | 12/2009 | Ortiz |
| 7,637,903 | B2 | 12/2009 | Lentz et al. |
| 7,648,519 | B2 | 1/2010 | Lee et al. |
| 7,650,742 | B2 | 1/2010 | Ushijima |
| 7,651,483 | B2 | 1/2010 | Byrum et al. |
| 7,651,509 | B2 | 1/2010 | Bojarski et al. |
| 7,654,431 | B2 | 2/2010 | Hueil et al. |
| 7,662,089 | B2 | 2/2010 | Okada et al. |
| 7,666,180 | B2 | 2/2010 | Holsten et al. |
| 7,666,203 | B2 | 2/2010 | Chanduszko et al. |
| 7,670,336 | B2 | 3/2010 | Young et al. |
| 7,674,259 | B2 | 3/2010 | Shadduck |
| 7,678,043 | B2 | 3/2010 | Gilad |
| 7,680,543 | B2 | 3/2010 | Azure |
| 7,684,599 | B2 | 3/2010 | Horn et al. |
| 7,686,826 | B2 | 3/2010 | Lee et al. |
| 7,697,970 | B2 | 4/2010 | Uchiyama et al. |
| 7,699,835 | B2 | 4/2010 | Lee et al. |
| 7,699,864 | B2 | 4/2010 | Kick et al. |
| 7,713,189 | B2 | 5/2010 | Hanke |
| 7,713,270 | B2 | 5/2010 | Suzuki |
| 7,736,374 | B2 | 6/2010 | Vaughan et al. |
| 7,744,615 | B2 | 6/2010 | Couture |
| 7,749,161 | B2 | 7/2010 | Beckman et al. |
| 7,753,933 | B2 | 7/2010 | Ginn et al. |
| 7,758,577 | B2 | 7/2010 | Nobis et al. |
| 7,762,949 | B2 | 7/2010 | Nakao |
| 7,762,998 | B2 | 7/2010 | Birk et al. |
| 7,763,012 | B2 | 7/2010 | Petrick et al. |
| 7,765,010 | B2 | 7/2010 | Chornenky et al. |
| 7,771,416 | B2 | 8/2010 | Spivey et al. |
| 7,771,437 | B2 | 8/2010 | Hogg et al. |
| 7,780,683 | B2 | 8/2010 | Roue et al. |
| 7,780,691 | B2 | 8/2010 | Stefanchik |
| 7,784,663 | B2 | 8/2010 | Shelton, IV |
| 7,794,409 | B2 | 9/2010 | Damarati |
| 7,794,475 | B2 | 9/2010 | Hess et al. |
| 7,798,386 | B2 | 9/2010 | Schall et al. |
| 7,828,186 | B2 | 11/2010 | Wales |
| 7,833,156 | B2 | 11/2010 | Williams et al. |
| 7,837,615 | B2 | 11/2010 | Le et al. |
| 7,842,028 | B2 | 11/2010 | Lee |

(56) References Cited

U.S. PATENT DOCUMENTS

| | | |
|---|---|---|
| 7,842,068 B2 | 11/2010 | Ginn |
| 7,846,171 B2 | 12/2010 | Kullas et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,867,216 B2 | 1/2011 | Wahr et al. |
| 7,879,004 B2 | 2/2011 | Seibel et al. |
| 7,887,530 B2 * | 2/2011 | Zemlok et al. .................... 606/1 |
| 7,892,220 B2 | 2/2011 | Faller et al. |
| 7,896,804 B2 | 3/2011 | Uchimura et al. |
| 7,896,887 B2 | 3/2011 | Rimbaugh et al. |
| 7,905,828 B2 | 3/2011 | Brock et al. |
| 7,909,809 B2 | 3/2011 | Scopton et al. |
| 7,914,513 B2 | 3/2011 | Voorhees, Jr. |
| 7,918,869 B2 | 4/2011 | Saadat et al. |
| 7,927,271 B2 | 4/2011 | Dimitriou et al. |
| 7,931,624 B2 | 4/2011 | Smith et al. |
| 7,945,332 B2 | 5/2011 | Schechter |
| 7,947,000 B2 | 5/2011 | Vargas et al. |
| 7,953,326 B2 | 5/2011 | Farr et al. |
| 7,955,298 B2 | 6/2011 | Carroll et al. |
| 7,963,975 B2 | 6/2011 | Criscuolo |
| 7,965,180 B2 | 6/2011 | Koyama |
| 7,967,808 B2 | 6/2011 | Fitzgerald et al. |
| 7,969,473 B2 | 6/2011 | Kotoda |
| 7,972,330 B2 | 7/2011 | Alejandro et al. |
| 7,976,552 B2 | 7/2011 | Suzuki |
| 7,985,239 B2 | 7/2011 | Suzuki |
| 7,988,685 B2 | 8/2011 | Ziaie et al. |
| 8,029,504 B2 | 10/2011 | Long |
| 8,034,046 B2 | 10/2011 | Eidenschink |
| 8,037,591 B2 | 10/2011 | Spivey et al. |
| 8,048,067 B2 | 11/2011 | Davalos et al. |
| 8,057,510 B2 | 11/2011 | Ginn et al. |
| 8,062,311 B2 | 11/2011 | Litscher et al. |
| 8,066,632 B2 | 11/2011 | Dario et al. |
| 8,075,587 B2 | 12/2011 | Ginn |
| 8,088,062 B2 | 1/2012 | Zwolinski |
| 8,096,459 B2 | 1/2012 | Ortiz et al. |
| 8,114,119 B2 | 2/2012 | Spivey et al. |
| 8,118,821 B2 | 2/2012 | Mouw |
| 8,147,424 B2 | 4/2012 | Kassab et al. |
| 8,157,813 B2 | 4/2012 | Ko et al. |
| 8,157,834 B2 | 4/2012 | Conlon |
| 8,172,772 B2 | 5/2012 | Zwolinski et al. |
| 8,182,414 B2 | 5/2012 | Handa et al. |
| 8,211,125 B2 | 7/2012 | Spivey |
| 8,221,310 B2 | 7/2012 | Saadat et al. |
| 8,241,204 B2 | 8/2012 | Spivey |
| 8,252,057 B2 | 8/2012 | Fox |
| 8,303,581 B2 | 11/2012 | Arts et al. |
| 8,430,811 B2 | 4/2013 | Hess et al. |
| 2001/0023333 A1 | 9/2001 | Wise et al. |
| 2001/0049497 A1 | 12/2001 | Kalloo et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0029055 A1 | 3/2002 | Bonutti |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0091391 A1 | 7/2002 | Cole et al. |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0165592 A1 | 11/2002 | Glukhovsky et al. |
| 2002/0173805 A1 | 11/2002 | Matsuno et al. |
| 2002/0183591 A1 | 12/2002 | Matsuura et al. |
| 2003/0014090 A1 | 1/2003 | Abrahamson |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0083681 A1 | 5/2003 | Moutafis et al. |
| 2003/0114731 A1 | 6/2003 | Cadeddu et al. |
| 2003/0114732 A1 | 6/2003 | Webler et al. |
| 2003/0120257 A1 | 6/2003 | Houston et al. |
| 2003/0124009 A1 | 7/2003 | Ravi et al. |
| 2003/0130564 A1 | 7/2003 | Martone et al. |
| 2003/0130656 A1 | 7/2003 | Levin |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0191497 A1 | 10/2003 | Cope |
| 2003/0195565 A1 | 10/2003 | Bonutti |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002683 A1 | 1/2004 | Nicholson et al. |
| 2004/0002735 A1 | 1/2004 | Lizardi et al. |
| 2004/0024414 A1 | 2/2004 | Downing |
| 2004/0034369 A1 | 2/2004 | Sauer et al. |
| 2004/0054322 A1 | 3/2004 | Vargas |
| 2004/0098007 A1 | 5/2004 | Heiss |
| 2004/0101456 A1 | 5/2004 | Kuroshima et al. |
| 2004/0104999 A1 | 6/2004 | Okada |
| 2004/0116948 A1 | 6/2004 | Sixto, Jr. et al. |
| 2004/0127940 A1 | 7/2004 | Ginn et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0161451 A1 | 8/2004 | Pierce et al. |
| 2004/0167545 A1 | 8/2004 | Sadler et al. |
| 2004/0176699 A1 | 9/2004 | Walker et al. |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0199159 A1 | 10/2004 | Lee et al. |
| 2004/0206859 A1 | 10/2004 | Chong et al. |
| 2004/0210245 A1 | 10/2004 | Erickson et al. |
| 2004/0215058 A1 | 10/2004 | Zirps et al. |
| 2004/0225183 A1 | 11/2004 | Michlitsch et al. |
| 2004/0225186 A1 | 11/2004 | Horne, Jr. et al. |
| 2004/0225323 A1 | 11/2004 | Nagase et al. |
| 2004/0230095 A1 | 11/2004 | Stefanchik et al. |
| 2004/0230096 A1 | 11/2004 | Stefanchik et al. |
| 2004/0230097 A1 | 11/2004 | Stefanchik et al. |
| 2004/0230161 A1 | 11/2004 | Zeiner |
| 2004/0243108 A1 | 12/2004 | Suzuki |
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2004/0254572 A1 | 12/2004 | McIntyre et al. |
| 2004/0260198 A1 | 12/2004 | Rothberg et al. |
| 2004/0260337 A1 | 12/2004 | Freed |
| 2005/0004515 A1 | 1/2005 | Hart et al. |
| 2005/0033265 A1 | 2/2005 | Engel et al. |
| 2005/0033277 A1 | 2/2005 | Clague et al. |
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0059963 A1 | 3/2005 | Phan et al. |
| 2005/0059964 A1 | 3/2005 | Fitz |
| 2005/0065397 A1 | 3/2005 | Saadat et al. |
| 2005/0065509 A1 | 3/2005 | Coldwell et al. |

(56) References Cited

U.S. PATENT DOCUMENTS

| | | |
|---|---|---|
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0080413 A1 | 4/2005 | Canady |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0096502 A1 | 5/2005 | Khalili |
| 2005/0101837 A1 | 5/2005 | Kalloo et al. |
| 2005/0101838 A1 | 5/2005 | Camillocci et al. |
| 2005/0101984 A1 | 5/2005 | Chanduszko et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0119613 A1 | 6/2005 | Moenning et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216033 A1* | 9/2005 | Lee et al. ................ 606/130 |
| 2005/0216050 A1 | 9/2005 | Sepetka et al. |
| 2005/0228224 A1 | 10/2005 | Okada et al. |
| 2005/0228406 A1 | 10/2005 | Bose |
| 2005/0234297 A1 | 10/2005 | Devierre et al. |
| 2005/0250983 A1 | 11/2005 | Tremaglio et al. |
| 2005/0250990 A1 | 11/2005 | Le et al. |
| 2005/0250993 A1 | 11/2005 | Jaeger |
| 2005/0251166 A1 | 11/2005 | Vaughan et al. |
| 2005/0251176 A1 | 11/2005 | Swanstrom et al. |
| 2005/0261674 A1 | 11/2005 | Nobis et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0274935 A1* | 12/2005 | Nelson ................ 254/226 |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0015131 A1 | 1/2006 | Kierce et al. |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1 | 2/2006 | Young et al. |
| 2006/0025812 A1 | 2/2006 | Shelton, IV |
| 2006/0025819 A1 | 2/2006 | Nobis et al. |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0058776 A1 | 3/2006 | Bilsbury |
| 2006/0064083 A1 | 3/2006 | Khalaj et al. |
| 2006/0069396 A1 | 3/2006 | Meade et al. |
| 2006/0069424 A1 | 3/2006 | Acosta et al. |
| 2006/0069425 A1 | 3/2006 | Hillis et al. |
| 2006/0069429 A1 | 3/2006 | Spence et al. |
| 2006/0074413 A1 | 4/2006 | Behzadian |
| 2006/0079890 A1 | 4/2006 | Guerra |
| 2006/0089528 A1 | 4/2006 | Tartaglia et al. |
| 2006/0095031 A1 | 5/2006 | Ormsby |
| 2006/0095060 A1 | 5/2006 | Mayenberger et al. |
| 2006/0100687 A1 | 5/2006 | Fahey et al. |
| 2006/0106423 A1 | 5/2006 | Weisel et al. |
| 2006/0111209 A1 | 5/2006 | Hinman et al. |
| 2006/0111210 A1 | 5/2006 | Hinman |
| 2006/0111704 A1 | 5/2006 | Brenneman et al. |
| 2006/0129166 A1 | 6/2006 | Lavelle |
| 2006/0135962 A1 | 6/2006 | Kick et al. |
| 2006/0135971 A1 | 6/2006 | Swanstrom et al. |
| 2006/0135984 A1 | 6/2006 | Kramer et al. |
| 2006/0142644 A1 | 6/2006 | Mulac et al. |
| 2006/0142652 A1 | 6/2006 | Keenan |
| 2006/0142790 A1 | 6/2006 | Gertner |
| 2006/0142798 A1 | 6/2006 | Holman et al. |
| 2006/0149131 A1 | 7/2006 | Or |
| 2006/0149132 A1 | 7/2006 | Iddan |
| 2006/0149135 A1 | 7/2006 | Paz |
| 2006/0161190 A1 | 7/2006 | Gadberry et al. |
| 2006/0167416 A1 | 7/2006 | Mathis et al. |
| 2006/0167482 A1 | 7/2006 | Swain et al. |
| 2006/0178560 A1 | 8/2006 | Saadat et al. |
| 2006/0183975 A1 | 8/2006 | Saadat et al. |
| 2006/0184161 A1 | 8/2006 | Maahs et al. |
| 2006/0189844 A1 | 8/2006 | Tien |
| 2006/0189845 A1 | 8/2006 | Maahs et al. |
| 2006/0190027 A1 | 8/2006 | Downey |
| 2006/0195084 A1 | 8/2006 | Slater |
| 2006/0200005 A1 | 9/2006 | Bjork et al. |
| 2006/0200121 A1 | 9/2006 | Mowery |
| 2006/0200169 A1 | 9/2006 | Sniffin |
| 2006/0200170 A1 | 9/2006 | Aranyi |
| 2006/0200199 A1 | 9/2006 | Bonutti et al. |
| 2006/0217665 A1 | 9/2006 | Prosek |
| 2006/0217697 A1 | 9/2006 | Lau et al. |
| 2006/0217742 A1 | 9/2006 | Messerly et al. |
| 2006/0217743 A1 | 9/2006 | Messerly et al. |
| 2006/0229639 A1 | 10/2006 | Whitfield |
| 2006/0229640 A1 | 10/2006 | Whitfield |
| 2006/0237022 A1 | 10/2006 | Chen et al. |
| 2006/0237023 A1 | 10/2006 | Cox et al. |
| 2006/0241570 A1 | 10/2006 | Wilk |
| 2006/0247500 A1 | 11/2006 | Voegele et al. |
| 2006/0247576 A1 | 11/2006 | Poncet |
| 2006/0247663 A1 | 11/2006 | Schwartz et al. |
| 2006/0247673 A1 | 11/2006 | Voegele et al. |
| 2006/0253004 A1 | 11/2006 | Frisch et al. |
| 2006/0253039 A1 | 11/2006 | McKenna et al. |
| 2006/0258907 A1 | 11/2006 | Stefanchik et al. |
| 2006/0258908 A1 | 11/2006 | Stefanchik et al. |
| 2006/0258910 A1 | 11/2006 | Stefanchik et al. |
| 2006/0258954 A1 | 11/2006 | Timberlake et al. |
| 2006/0258955 A1 | 11/2006 | Hoffman et al. |
| 2006/0259010 A1 | 11/2006 | Stefanchik et al. |
| 2006/0259073 A1 | 11/2006 | Miyamoto et al. |
| 2006/0264752 A1 | 11/2006 | Rubinsky et al. |
| 2006/0264904 A1 | 11/2006 | Kerby et al. |
| 2006/0264930 A1 | 11/2006 | Nishimura |
| 2006/0270902 A1 | 11/2006 | Igarashi et al. |
| 2006/0271042 A1 | 11/2006 | Latterell et al. |
| 2006/0271102 A1 | 11/2006 | Bosshard et al. |
| 2006/0276835 A1 | 12/2006 | Uchida |
| 2006/0281970 A1 | 12/2006 | Stokes et al. |
| 2006/0282106 A1 | 12/2006 | Cole et al. |

(56) References Cited

U.S. PATENT DOCUMENTS

| | | |
|---|---|---|
| 2006/0285732 A1 | 12/2006 | Horn et al. |
| 2006/0287644 A1 | 12/2006 | Inganas et al. |
| 2006/0287666 A1 | 12/2006 | Saadat et al. |
| 2006/0293626 A1 | 12/2006 | Byrum et al. |
| 2007/0002135 A1 | 1/2007 | Glukhovsky |
| 2007/0005019 A1 | 1/2007 | Okishige |
| 2007/0010801 A1 | 1/2007 | Chen et al. |
| 2007/0015965 A1 | 1/2007 | Cox et al. |
| 2007/0016225 A1 | 1/2007 | Nakao |
| 2007/0027469 A1* | 2/2007 | Smith et al. ............ 606/205 |
| 2007/0032700 A1 | 2/2007 | Fowler et al. |
| 2007/0032701 A1 | 2/2007 | Fowler et al. |
| 2007/0043261 A1 | 2/2007 | Watanabe et al. |
| 2007/0043345 A1 | 2/2007 | Davalos et al. |
| 2007/0049800 A1 | 3/2007 | Boulais |
| 2007/0049902 A1 | 3/2007 | Griffin et al. |
| 2007/0051375 A1 | 3/2007 | Milliman |
| 2007/0060880 A1 | 3/2007 | Gregorich et al. |
| 2007/0066869 A1 | 3/2007 | Hoffman |
| 2007/0067017 A1 | 3/2007 | Trapp |
| 2007/0073102 A1 | 3/2007 | Matsuno et al. |
| 2007/0073269 A1 | 3/2007 | Becker |
| 2007/0079924 A1 | 4/2007 | Saadat et al. |
| 2007/0083195 A1 | 4/2007 | Werneth et al. |
| 2007/0088370 A1 | 4/2007 | Kahle et al. |
| 2007/0100375 A1 | 5/2007 | Mikkaichi et al. |
| 2007/0100376 A1 | 5/2007 | Mikkaichi et al. |
| 2007/0106118 A1 | 5/2007 | Moriyama |
| 2007/0106317 A1 | 5/2007 | Shelton, IV et al. |
| 2007/0112251 A1 | 5/2007 | Nakhuda |
| 2007/0112331 A1 | 5/2007 | Weber et al. |
| 2007/0112342 A1 | 5/2007 | Pearson et al. |
| 2007/0112383 A1 | 5/2007 | Conlon et al. |
| 2007/0112384 A1 | 5/2007 | Conlon et al. |
| 2007/0112385 A1 | 5/2007 | Conlon |
| 2007/0112417 A1 | 5/2007 | Shanley et al. |
| 2007/0112425 A1 | 5/2007 | Schaller et al. |
| 2007/0118115 A1 | 5/2007 | Artale et al. |
| 2007/0123840 A1 | 5/2007 | Cox |
| 2007/0129605 A1 | 6/2007 | Schaaf |
| 2007/0129719 A1 | 6/2007 | Kendale et al. |
| 2007/0129760 A1 | 6/2007 | Demarais et al. |
| 2007/0135709 A1 | 6/2007 | Rioux et al. |
| 2007/0135803 A1 | 6/2007 | Belson |
| 2007/0142706 A1 | 6/2007 | Matsui et al. |
| 2007/0142710 A1 | 6/2007 | Yokoi et al. |
| 2007/0142780 A1 | 6/2007 | Van Lue |
| 2007/0154460 A1 | 7/2007 | Kraft et al. |
| 2007/0156028 A1 | 7/2007 | Van Lue et al. |
| 2007/0156127 A1 | 7/2007 | Rioux et al. |
| 2007/0161855 A1 | 7/2007 | Mikkaichi et al. |
| 2007/0162101 A1 | 7/2007 | Burgermeister et al. |
| 2007/0167901 A1 | 7/2007 | Herrig et al. |
| 2007/0173691 A1 | 7/2007 | Yokoi et al. |
| 2007/0173869 A1 | 7/2007 | Gannoe et al. |
| 2007/0173870 A2 | 7/2007 | Zacharias |
| 2007/0173872 A1 | 7/2007 | Neuenfeldt |
| 2007/0179525 A1 | 8/2007 | Frecker et al. |
| 2007/0179530 A1 | 8/2007 | Tieu et al. |
| 2007/0197865 A1 | 8/2007 | Miyake et al. |
| 2007/0198057 A1 | 8/2007 | Gelbart et al. |
| 2007/0203398 A1 | 8/2007 | Bonadio et al. |
| 2007/0203487 A1 | 8/2007 | Sugita |
| 2007/0208336 A1 | 9/2007 | Kim et al. |
| 2007/0208364 A1 | 9/2007 | Smith et al. |
| 2007/0213754 A1 | 9/2007 | Mikkaichi et al. |
| 2007/0225554 A1 | 9/2007 | Maseda et al. |
| 2007/0233040 A1 | 10/2007 | Macnamara et al. |
| 2007/0244358 A1 | 10/2007 | Lee |
| 2007/0250038 A1 | 10/2007 | Boulais |
| 2007/0250057 A1 | 10/2007 | Nobis et al. |
| 2007/0255096 A1 | 11/2007 | Stefanchik et al. |
| 2007/0255100 A1 | 11/2007 | Barlow et al. |
| 2007/0255273 A1 | 11/2007 | Fernandez et al. |
| 2007/0255303 A1 | 11/2007 | Bakos et al. |
| 2007/0255306 A1 | 11/2007 | Conlon et al. |
| 2007/0260112 A1 | 11/2007 | Rahmani |
| 2007/0260117 A1 | 11/2007 | Zwolinski et al. |
| 2007/0260121 A1 | 11/2007 | Bakos et al. |
| 2007/0260242 A1 | 11/2007 | Dycus et al. |
| 2007/0260273 A1 | 11/2007 | Cropper et al. |
| 2007/0260302 A1 | 11/2007 | Igaki |
| 2007/0270629 A1 | 11/2007 | Charles |
| 2007/0270889 A1 | 11/2007 | Conlon et al. |
| 2007/0270895 A1 | 11/2007 | Nobis et al. |
| 2007/0270907 A1 | 11/2007 | Stokes et al. |
| 2007/0282165 A1 | 12/2007 | Hopkins et al. |
| 2007/0282371 A1 | 12/2007 | Lee et al. |
| 2007/0293727 A1 | 12/2007 | Goldfarb et al. |
| 2007/0299387 A1 | 12/2007 | Williams et al. |
| 2008/0004650 A1 | 1/2008 | George |
| 2008/0015409 A1 | 1/2008 | Barlow et al. |
| 2008/0015413 A1 | 1/2008 | Barlow et al. |
| 2008/0015552 A1 | 1/2008 | Doyle et al. |
| 2008/0021416 A1 | 1/2008 | Arai et al. |
| 2008/0022927 A1 | 1/2008 | Zhang et al. |
| 2008/0027387 A1 | 1/2008 | Grabinsky |
| 2008/0033451 A1 | 2/2008 | Rieber et al. |
| 2008/0051629 A1 | 2/2008 | Sugiyama et al. |
| 2008/0051735 A1 | 2/2008 | Measamer et al. |
| 2008/0058586 A1 | 3/2008 | Karpiel |
| 2008/0058854 A1 | 3/2008 | Kieturakis et al. |
| 2008/0065169 A1 | 3/2008 | Colliou et al. |
| 2008/0071264 A1 | 3/2008 | Azure |
| 2008/0086172 A1 | 4/2008 | Martin et al. |
| 2008/0097159 A1 | 4/2008 | Ishiguro |
| 2008/0097472 A1 | 4/2008 | Agmon et al. |
| 2008/0097483 A1 | 4/2008 | Ortiz et al. |
| 2008/0103527 A1 | 5/2008 | Martin et al. |
| 2008/0114384 A1 | 5/2008 | Chang et al. |
| 2008/0119870 A1 | 5/2008 | Williams |
| 2008/0119891 A1 | 5/2008 | Miles et al. |
| 2008/0125796 A1 | 5/2008 | Graham |
| 2008/0132892 A1 | 6/2008 | Lunsford et al. |
| 2008/0139882 A1 | 6/2008 | Fujimori |
| 2008/0140069 A1 | 6/2008 | Filloux et al. |
| 2008/0140071 A1 | 6/2008 | Vegesna |
| 2008/0147113 A1 | 6/2008 | Nobis et al. |
| 2008/0171907 A1 | 7/2008 | Long et al. |
| 2008/0177135 A1 | 7/2008 | Muyari et al. |
| 2008/0188710 A1 | 8/2008 | Segawa et al. |
| 2008/0188868 A1 | 8/2008 | Weitzner et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200912 A1 | 8/2008 | Long |
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0221587 A1 | 9/2008 | Schwartz |
| 2008/0221619 A1 | 9/2008 | Spivey et al. |
| 2008/0228213 A1 | 9/2008 | Blakeney et al. |
| 2008/0230972 A1 | 9/2008 | Ganley |
| 2008/0234696 A1 | 9/2008 | Taylor et al. |
| 2008/0243106 A1 | 10/2008 | Coe et al. |
| 2008/0243148 A1 | 10/2008 | Mikkaichi et al. |
| 2008/0243176 A1 | 10/2008 | Weitzner et al. |
| 2008/0249567 A1 | 10/2008 | Kaplan |
| 2008/0262513 A1 | 10/2008 | Stahler et al. |
| 2008/0262524 A1 | 10/2008 | Bangera et al. |
| 2008/0262540 A1 | 10/2008 | Bangera et al. |
| 2008/0269782 A1 | 10/2008 | Stefanchik et al. |
| 2008/0269783 A1 | 10/2008 | Griffith |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0287983 A1 | 11/2008 | Smith et al. |
| 2008/0300461 A1 | 12/2008 | Shaw et al. |
| 2008/0300547 A1 | 12/2008 | Bakos |
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |

(56) References Cited

U.S. PATENT DOCUMENTS

| | | |
|---|---|---|
| 2008/0319436 A1 | 12/2008 | Daniel et al. |
| 2008/0319439 A1 | 12/2008 | Ootsubu |
| 2009/0005636 A1 | 1/2009 | Pang et al. |
| 2009/0054728 A1 | 2/2009 | Trusty |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0078736 A1 | 3/2009 | Van Lue |
| 2009/0082776 A1 | 3/2009 | Cresina |
| 2009/0082779 A1 | 3/2009 | Nakao |
| 2009/0112059 A1 | 4/2009 | Nobis |
| 2009/0112062 A1 | 4/2009 | Bakos |
| 2009/0112063 A1 | 4/2009 | Bakos et al. |
| 2009/0125042 A1 | 5/2009 | Mouw |
| 2009/0131751 A1 | 5/2009 | Spivey et al. |
| 2009/0131932 A1 | 5/2009 | Vakharia et al. |
| 2009/0131933 A1 | 5/2009 | Ghabrial et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0143818 A1 | 6/2009 | Faller et al. |
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0192534 A1 | 7/2009 | Ortiz et al. |
| 2009/0198231 A1 | 8/2009 | Esser et al. |
| 2009/0198253 A1 | 8/2009 | Omori |
| 2009/0210000 A1 | 8/2009 | Sullivan et al. |
| 2009/0216248 A1 | 8/2009 | Uenohara et al. |
| 2009/0221873 A1 | 9/2009 | McGrath |
| 2009/0227828 A1 | 9/2009 | Swain et al. |
| 2009/0228001 A1 | 9/2009 | Pacey |
| 2009/0248055 A1 | 10/2009 | Spivey et al. |
| 2009/0259105 A1 | 10/2009 | Miyano et al. |
| 2009/0269317 A1 | 10/2009 | Davalos |
| 2009/0281559 A1 | 11/2009 | Swain et al. |
| 2009/0287206 A1 | 11/2009 | Jun |
| 2009/0287236 A1 | 11/2009 | Bakos et al. |
| 2009/0292164 A1 | 11/2009 | Yamatani |
| 2009/0299135 A1 | 12/2009 | Spivey |
| 2009/0299362 A1 | 12/2009 | Long et al. |
| 2009/0299385 A1 | 12/2009 | Stefanchik et al. |
| 2009/0299406 A1 | 12/2009 | Swain et al. |
| 2009/0299409 A1 | 12/2009 | Coe et al. |
| 2009/0306658 A1 | 12/2009 | Nobis et al. |
| 2009/0306683 A1 | 12/2009 | Zwolinski et al. |
| 2009/0322864 A1 | 12/2009 | Karasawa et al. |
| 2009/0326332 A1 | 12/2009 | Carter |
| 2009/0326561 A1 | 12/2009 | Carroll, II et al. |
| 2010/0010294 A1 | 1/2010 | Conlon et al. |
| 2010/0010298 A1 | 1/2010 | Bakos et al. |
| 2010/0010299 A1 | 1/2010 | Bakos et al. |
| 2010/0010303 A1 | 1/2010 | Bakos |
| 2010/0010510 A1 | 1/2010 | Stefanchik |
| 2010/0010511 A1 | 1/2010 | Harris et al. |
| 2010/0023032 A1 | 1/2010 | Granja Filho |
| 2010/0030211 A1 | 2/2010 | Davalos et al. |
| 2010/0036198 A1 | 2/2010 | Tacchino et al. |
| 2010/0042045 A1 | 2/2010 | Splvey |
| 2010/0048990 A1 | 2/2010 | Bakos |
| 2010/0049190 A1 | 2/2010 | Long et al. |
| 2010/0049223 A1 | 2/2010 | Granja Filho |
| 2010/0056862 A1 | 3/2010 | Bakos |
| 2010/0056864 A1 | 3/2010 | Lee |
| 2010/0057085 A1 | 3/2010 | Holcomb et al. |
| 2010/0057108 A1 | 3/2010 | Spivey et al. |
| 2010/0076451 A1 | 3/2010 | Zwolinski et al. |
| 2010/0076460 A1* | 3/2010 | Taylor et al. ............... 606/144 |
| 2010/0081877 A1 | 4/2010 | Vakharia |
| 2010/0091128 A1 | 4/2010 | Ogasawara et al. |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0130975 A1 | 5/2010 | Long |
| 2010/0152539 A1 | 6/2010 | Ghabrial et al. |
| 2010/0152746 A1 | 6/2010 | Ceniccola et al. |
| 2010/0179510 A1 | 7/2010 | Fox et al. |
| 2010/0179530 A1 | 7/2010 | Long et al. |
| 2010/0191050 A1 | 7/2010 | Zwolinski |
| 2010/0191267 A1 | 7/2010 | Fox |
| 2010/0198149 A1 | 8/2010 | Fox |
| 2010/0198248 A1 | 8/2010 | Vakharia |
| 2010/0217367 A1 | 8/2010 | Belson |
| 2010/0249700 A1 | 9/2010 | Spivey |
| 2010/0261994 A1 | 10/2010 | Davalos et al. |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2010/0331758 A1 | 12/2010 | Davalos et al. |
| 2011/0077476 A1 | 3/2011 | Rofougaran |
| 2011/0093009 A1 | 4/2011 | Fox |
| 2011/0098694 A1 | 4/2011 | Long |
| 2011/0098704 A1 | 4/2011 | Long et al. |
| 2011/0105850 A1 | 5/2011 | Voegele et al. |
| 2011/0106221 A1 | 5/2011 | Neal, II et al. |
| 2011/0112434 A1 | 5/2011 | Ghabrial et al. |
| 2011/0115891 A1 | 5/2011 | Trusty |
| 2011/0124964 A1 | 5/2011 | Nobis |
| 2011/0152609 A1 | 6/2011 | Trusty et al. |
| 2011/0152610 A1 | 6/2011 | Trusty et al. |
| 2011/0152612 A1 | 6/2011 | Trusty et al. |
| 2011/0152858 A1 | 6/2011 | Long et al. |
| 2011/0152859 A1 | 6/2011 | Long et al. |
| 2011/0152878 A1 | 6/2011 | Trusty et al. |
| 2011/0152923 A1 | 6/2011 | Fox |
| 2011/0160514 A1 | 6/2011 | Long et al. |
| 2011/0190659 A1 | 8/2011 | Long et al. |
| 2011/0190764 A1 | 8/2011 | Long et al. |
| 2011/0193948 A1 | 8/2011 | Amling et al. |
| 2011/0245619 A1 | 10/2011 | Holcomb |
| 2011/0285488 A1 | 11/2011 | Scott et al. |
| 2011/0306971 A1 | 12/2011 | Long |
| 2012/0004502 A1 | 1/2012 | Weitzner et al. |
| 2012/0029335 A1 | 2/2012 | Sudam et al. |
| 2012/0088965 A1 | 4/2012 | Stokes et al. |
| 2012/0089089 A1 | 4/2012 | Swain et al. |
| 2012/0089093 A1 | 4/2012 | Trusty |
| 2012/0116155 A1 | 5/2012 | Trusty |
| 2012/0179148 A1 | 7/2012 | Conlon |
| 2012/0191075 A1 | 7/2012 | Trusty |
| 2012/0191076 A1 | 7/2012 | Voegele et al. |
| 2012/0220998 A1 | 8/2012 | Long et al. |
| 2012/0220999 A1 | 8/2012 | Long |
| 2012/0221002 A1 | 8/2012 | Long et al. |
| 2012/0238796 A1 | 9/2012 | Conlon |
| 2012/0330306 A1 | 12/2012 | Long et al. |
| 2013/0090666 A1 | 4/2013 | Hess et al. |

FOREIGN PATENT DOCUMENTS

| | | | |
|---|---|---|---|
| DE | 4323585 | A1 | 1/1995 |
| DE | 19713797 | A1 | 10/1997 |
| DE | 19757056 | B4 | 8/2008 |
| DE | 102006027873 | B4 | 10/2009 |
| EP | 0086338 | A1 | 8/1983 |
| EP | 0286415 | A2 | 10/1988 |
| EP | 0589454 | A2 | 3/1994 |
| EP | 0464479 | B1 | 3/1995 |
| EP | 0529675 | B1 | 2/1996 |
| EP | 0621009 | B1 | 7/1997 |
| EP | 0724863 | B1 | 7/1999 |
| EP | 0760629 | B1 | 11/1999 |
| EP | 0818974 | B1 | 7/2001 |
| EP | 1281356 | A2 | 2/2003 |
| EP | 0947166 | B1 | 5/2003 |
| EP | 0836832 | B1 | 12/2003 |
| EP | 1402837 | A1 | 3/2004 |
| EP | 0744918 | B1 | 4/2004 |
| EP | 0931515 | B1 | 8/2004 |

(56) References Cited

FOREIGN PATENT DOCUMENTS

| | | |
|---|---|---|
| EP | 0941128 B1 | 10/2004 |
| EP | 1411843 B1 | 10/2004 |
| EP | 1150614 B1 | 11/2004 |
| EP | 1477104 A1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |
| EP | 1452143 B1 | 9/2005 |
| EP | 1616527 A2 | 1/2006 |
| EP | 1006888 B1 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1582138 B1 | 9/2008 |
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 0723462 B1 | 3/2009 |
| EP | 1769749 B1 | 11/2009 |
| EP | 2135545 A2 | 12/2009 |
| EP | 1493397 B1 | 9/2011 |
| FR | 2731610 A1 | 9/1996 |
| GB | 330629 A | 6/1930 |
| GB | 2335860 A | 10/1999 |
| GB | 2403909 A | 1/2005 |
| GB | 2421190 A | 6/2006 |
| GB | 2443261 A | 4/2008 |
| JP | 56-46674 | 4/1981 |
| JP | 63309252 A | 12/1988 |
| JP | 4038960 A | 2/1992 |
| JP | 8-29699 A | 2/1996 |
| JP | 2000245683 A | 9/2000 |
| JP | 2002-369791 A | 12/2002 |
| JP | 2003-088494 A | 3/2003 |
| JP | 2003-235852 | 8/2003 |
| JP | 2003-235852 A | 8/2003 |
| JP | 2004-33525 A | 2/2004 |
| JP | 2004-065745 A | 3/2004 |
| JP | 2005-121947 A | 5/2005 |
| JP | 2005-261514 A | 9/2005 |
| JP | 2006297005 A | 11/2006 |
| JP | 2006-343510 A | 12/2006 |
| NL | 1021295 C2 | 2/2004 |
| SU | 194230 | 5/1967 |
| SU | 980703 | 12/1982 |
| WO | WO 84/01707 A1 | 5/1984 |
| WO | WO 92/13494 A1 | 8/1992 |
| WO | WO 93/10850 A1 | 6/1993 |
| WO | WO 93/20760 A1 | 10/1993 |
| WO | WO 93/20765 A1 | 10/1993 |
| WO | WO 95/09666 A1 | 4/1995 |
| WO | WO 96/22056 A1 | 7/1996 |
| WO | WO 96/27331 A1 | 9/1996 |
| WO | WO 96/39946 A1 | 12/1996 |
| WO | WO 97/12557 A1 | 4/1997 |
| WO | WO 98/01080 A1 | 1/1998 |
| WO | WO 99/00060 A1 | 1/1999 |
| WO | WO 99/09919 A1 | 3/1999 |
| WO | WO 99/17661 A1 | 4/1999 |
| WO | WO 99/30622 A2 | 6/1999 |
| WO | WO 00/35358 A1 | 6/2000 |
| WO | WO 00/68665 A1 | 11/2000 |
| WO | WO 01/10319 A1 | 2/2001 |
| WO | WO 01/26708 A1 | 4/2001 |
| WO | WO 01/41627 A2 | 6/2001 |
| WO | WO 01/58360 A1 | 8/2001 |
| WO | WO 02/11621 A1 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/081761 A2 | 10/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/037149 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2005/122866 A1 | 12/2005 |
| WO | WO 2006/007399 A1 | 1/2006 |
| WO | WO 2006/012630 A1 | 2/2006 |
| WO | WO 2006/040109 A1 | 4/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/013059 A2 | 2/2007 |
| WO | WO 2007/014063 A2 | 2/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2007/143200 A2 | 12/2007 |
| WO | WO 2007/144004 A1 | 12/2007 |
| WO | WO 2008/005433 A1 | 1/2008 |
| WO | WO 2008/033356 A2 | 3/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/079440 A2 | 7/2008 |
| WO | WO 2008/101075 A2 | 8/2008 |
| WO | WO 2008/102154 A2 | 8/2008 |
| WO | WO 2008/108863 A2 | 9/2008 |
| WO | WO 2008/151237 A1 | 12/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/036457 A1 | 3/2009 |
| WO | WO 2009/121017 A1 | 10/2009 |
| WO | WO 2010/027688 A1 | 3/2010 |
| WO | WO 2010/056716 A2 | 5/2010 |
| WO | WO 2010/080974 A1 | 7/2010 |
| WO | WO 2010/088481 A1 | 8/2010 |

OTHER PUBLICATIONS

Michael S. Kavic, M.D., "Natural Orifice Translumenal Endoscopic Surgery: "Notes"", JSLS, vol. 10, pp. 133-134 (2006).

Ethicon, Inc., "Wound Closure Manual: Chapter 3 (The Surgical Needle)," 15 pages, (publication date unknown).

Guido M. Sclabas, M.D., et al., "Endoluminal Methods for Gastrotomy Closure in Natural Orifice TransEnteric Surgery (Notes)," Surgical Innovation, vol. 13, No. 1, pp. 23-30, Mar. 2006.

(56) References Cited

OTHER PUBLICATIONS

Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastroint Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Endosc., vol. 8, pp. 28-32, 2006.
"Z-Offset Technique Used in the Introduction of Trocar During Laparoscopic Surgery," M.S. Hershey Notes Presentation to EES Notes Development Team, Sep. 27, 2007.
F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).
I. Fraser, "An Historical Perspective on Mechanical Aids in Intestinal Anastamosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Intery Radiol, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastroint Endosc, (2001), vol. 53, pp. 780-784.
H. Okajima et al., "Magnet Compression Anastamosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutrues," Dis col. Rectum, (1963), vol. 5, pp. 98-101.
T. Hardy, Jr., M.D. et al., "A Biofragmentable Ring for Sutureless Bowel Anastomosis. An Experimental Study," Dis col. Rectum, (1985), vol. 28, pp. 484-490.
P. O'Neill, M.D. et al., "Nonsuture Intestinal Anastomosis," Am J. Surg, (1962), vol. 104, pp. 761-767.

C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
USGI® EndoSurgical Operating System—g-Prox® Tissue Grasper/ Approximation Device; [online] URL: http://www.usgimedical.com/eos/components-gprox.htm—accessed May 30, 2008 (2 pages).
Printout of web page—http://www.vacumed.com/zcom/product/ Product.do?compid=27&prodid=852, #51XX Low-Cost Permanent Tubes 2MM ID, Smooth Interior Walls, VacuMed, Ventura, California, Accessed Jul. 24, 2007.
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ERCP; Jackson Siegelbaum Gastroenterology; [online] URL: http://www.gicare.com/pated/epdgs20.htm; accessed Feb. 21, 2008 (3 pages).
D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, Aug. (2007), pp. 255-259.
D.B. Nelson, MD et al., "Endoscopic Hemostatic Devices," Gastrointestinal Endoscopy, vol. 54, No. 6, 2001, pp. 833-840.
U.S. Appl. No. 11/744,271, filed May 4, 2007.
U.S. Appl. No. 11/744,279, filed May 4, 2007.
U.S. Appl. No. 11/796,035, filed Apr. 26, 2007.
U.S. Appl. No. 11/796,357, filed Apr. 27, 2007.
U.S. Appl. No. 11/894,358, filed Aug. 21, 2007.
U.S. Appl. No. 11/897,676, filed Aug. 31, 2007.
U.S. Appl. No. 11/968,810, filed Jan. 3, 2008.
U.S. Appl. No. 11/981,070, filed Oct. 31, 2007.
U.S. Appl. No. 11/981,078, filed Oct. 31, 2007.
U.S. Appl. No. 11/981,134, filed Oct. 31, 2007.
U.S. Appl. No. 11/986,084, filed Nov. 20, 2007.
U.S. Appl. No. 11/986,420, filed Nov. 21, 2007.
U.S. Appl. No. 11/986,489, filed Nov. 21, 2007.
U.S. Appl. No. 11/998,370, filed Nov. 29, 2007.
U.S. Appl. No. 12/014,417, filed Jan. 5, 2008.
U.S. Appl. No. 12/019,461, filed Jan. 24, 2008.
U.S. Appl. No. 12/045,318, filed Mar. 10, 2008.
U.S. Appl. No. 12/109,673, filed Apr. 25, 2008.
U.S. Appl. No. 12/109,699, filed Apr. 25, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/130,010, filed May 30, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 11/762,855, filed Jun. 14, 2007.
U.S. Appl. No. 12/192,372, filed Aug. 15, 2008.
U.S. Appl. No. 12/203,330, filed Sep. 3, 2008.
U.S. Appl. No. 12/197,749, filed Aug. 25, 2008.
U.S. Appl. No. 12/197,653, filed Aug. 25, 2008.
U.S. Appl. No. 12/202,740, filed Sep. 2, 2008.
U.S. Appl. No. 12/203,458, filed Sep. 3, 2008.
U.S. Appl. No. 12/201,812, filed Aug. 29, 2008.
U.S. Appl. No. 12/207,306, filed Sep. 9, 2008.
U.S. Appl. No. 12/243,334, filed Oct. 1, 2008.
U.S. Appl. No. 12/234,425, filed Sep. 19, 2008.

(56) References Cited

OTHER PUBLICATIONS

International Search Report and Written Opinion for PCT/US2009/045588, Dec. 11, 2009 (20 pages).
CRE™ Pulmonary Balloon Dilator; [online] URL: http://www.bostonscientific.com/Device.bsci?page=HCP_Overview&navRelId=1000.1003&method=D . . ., accessed Jul. 18, 2008 (4 pages).
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).
D. Wilhelm et al., "An Innovative, Safe and Sterile Sigmoid Access (ISSA) for Notes," Endoscopy 2007, vol. 39, pp. 401-406.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklavčič et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and cathether-delivered therapies for colorectal liver metastases (CRLM)," EJSO, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).
Heller et al., "Electrically mediated plasmid DNA delivery to hepatocellular carcinomas in vivo," Gene Therapy, 7, pp. 826-829 (2000).
Widera et al., "Increased DNA Vaccine Delivery and Immunogenicity by Electroporation In Vivo," The Journal of Immunology, 164, pp. 4635-4640 (2000).
Weaver et al., "Theory of electroporation: A review," Bioelectrochemistry and Bioenergetics, 41, pp. 135-160 (1996).
Mulier et al., "Radiofrequency Ablation Versus Resection for Resectable Colorectal Liver Metastases: Time for a Randomized Trial?" Annals of Surgical Oncology, 15(1), pp. 144-157 (2008).
Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).
Guyton et al., "Membrane Potentials and Action Potentials," W.B. Sanders, ed. Textbook of Medical Physiology, p. 56 (2000).
Guyton et al., "Contraction of Skeletal Muscle," Textbook of Medical Physiology, pp. 82-84 (2000).
"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).
"Ethicon Endo-Surgery Studies Presented at DDW Demonstrate Potential of Pure Notes Surgery With Company's Toolbox," Jun. 3, 2009 Press Release; URL http://www.jnj.com/connect/news/product/20090603_120000; accessed Aug. 28, 2009 (3 pages).
Castellvi et al., "Hybrid Transvaginal Notes Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).
Castellvi et al., "Hybrid Transvaginal Notes Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).
U.S. Appl. No. 12/277,975, filed Nov. 25, 2008.
U.S. Appl. No. 12/277,957, filed Nov. 25, 2008.
U.S. Appl. No. 12/332,938, filed Dec. 11, 2008.
U.S. Appl. No. 12/337,340, filed Dec. 17, 2008.
U.S. Appl. No. 12/352,451, filed Jan. 12, 2009.
U.S. Appl. No. 12/359,824, filed Jan. 26, 2009.
U.S. Appl. No. 12/352,375, filed Jan. 12, 2009.
U.S. Appl. No. 12/359,053, filed Jan. 23, 2009.
U.S. Appl. No. 12/362,826, filed Jan. 30, 2009.
U.S. Appl. No. 12/363,137, filed Jan. 30, 2009.
U.S. Appl. No. 12/364,172, filed Feb. 2, 2009.
U.S. Appl. No. 12/364,256, filed Feb. 2, 2009.
U.S. Appl. No. 12/413,479, filed Mar. 27, 2009.
U.S. Appl. No. 12/468,462, filed May 19, 2009.
U.S. Appl. No. 12/607,252, filed Oct. 28, 2009.
U.S. Appl. No. 12/580,400, filed Oct. 16, 2009.
U.S. Appl. No. 12/607,388, filed Oct. 28, 2009.
U.S. Appl. No. 12/612,911, filed Nov. 5, 2009.
U.S. Appl. No. 12/614,143, filed Nov. 6, 2009.
U.S. Appl. No. 12/617,998, filed Nov. 13, 2009.
U.S. Appl. No. 12/635,298, filed Dec. 10, 2009.
U.S. Appl. No. 12/640,440, filed Dec. 17, 2009.
U.S. Appl. No. 12/640,469, filed Dec. 17, 2009.
U.S. Appl. No. 12/640,476, filed Dec. 17, 2009.
U.S. Appl. No. 12/640,492, filed Dec. 17, 2009.
U.S. Appl. No. 12/641,823, filed Dec. 18, 2009.
U.S. Appl. No. 12/641,853, filed Dec. 18, 2009.
U.S. Appl. No. 12/641,837, filed Dec. 18, 2009.
U.S. Appl. No. 12/651,181, filed Dec. 31, 2009.
OCTO Port Modular Laparoscopy System for Single Incision Access, Jan. 4, 2010; URL http://www.medgadget.com/archives/2010/01/octo_port_modular_laparo . . . ; accessed Jan. 5, 2010 (4 pages).
Hakko Retractors, obtained Aug. 25, 2009 (5 pages).
Zadno et al,, "Linear Superelasticity in Cold-Worked NI-TI," Engineering Aspects of Shape Memory Alloys, pp. 414-419 (1990).
How Stuff Works "How Smart Structures Will Work," http://science.howstuffworks.com/engineering/structural/smart-structure1.htm; accessed online Nov. 1, 2011 (3 pages).
Instant Armor: Science Videos—Science News—ScienCentral; http://www.sciencentral.com/articles./view.php3?article_id=218392121; accessed online Nov. 1, 2011 (2 pages).
Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).
Jolly et al., Properties and Applications of Commercial Magnetorheological Fluids. SPIE 5th Annual Int. Symposium on Smart Structures and Materials, 1998 (18 pages).
U.S. Appl. No. 13/267,251, filed Oct. 6, 2011.
U.S. Appl. No. 13/325,791, filed Dec. 14, 2011.
U.S. Appl. No. 13/399,358, filed Feb. 17, 2012.
U.S. Appl. No. 13/420,818, filed Mar. 15, 2012.
Bewlay et al., "Spinning" in ASM Handbook, vol. 14B, Metalworking: Sheet Forming (2006).

\* cited by examiner

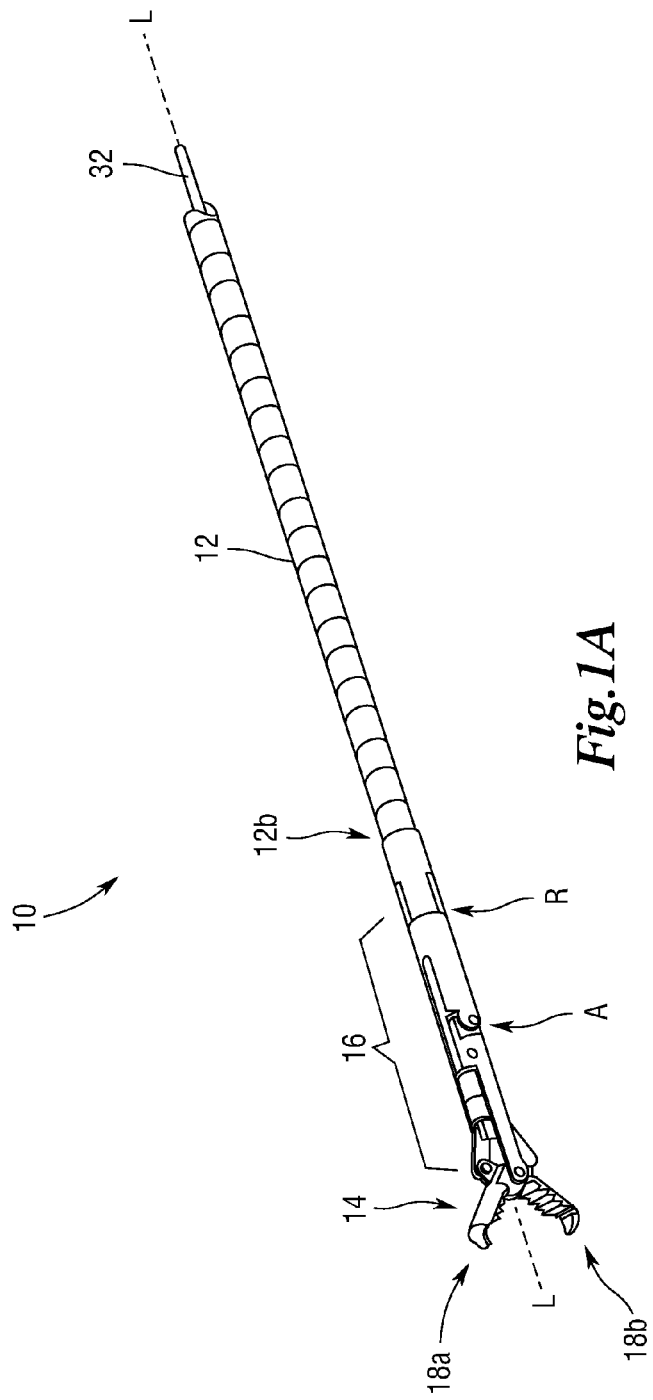

ACTUATING AND ARTICULATING SURGICAL DEVICE

BACKGROUND

In laparoscopic surgical procedures, a small incision is made in the body and an elongate shaft of a surgical device is inserted through the incision to position a distal end of the shaft at a surgical site. In endoscopic procedures, the elongate shaft of a surgical device is inserted through a natural orifice, such as the mouth, vagina, or anus, and is advanced along a pathway to position a distal end of the device at a surgical site. Endoscopic procedures typically require the use of a flexible shaft to accommodate the tortuous pathway of the body lumen, whereas rigid shafts can be used in laparoscopic procedures. These tools can be used to engage and/or treat tissue in a number of ways to achieve a diagnostic or therapeutic effect.

Many current laparoscopic and endoscopic devices utilize articulating effectors to provide the user with more control over the orientation of the working end of the instrument. Integration of the controls for articulating, as well as actuating, a working end of a laparoscopic or endoscopic device tends to be complicated by the size constraints of the relatively small pathway through which it is inserted. The controls for an endoscopic device are further complicated by the flexibility of the shaft. Generally, the control motions are all transferred through the shaft as longitudinal translations, which can interfere with the flexibility of the shaft. Also, the control motion to actuate one aspect of the device may inadvertently cause actuation of a second aspect of the device. For instance, the application of force to actuate (i.e., fire, open and close, energize, etc.) the end effector might also cause undesirable articulation or "hinging" of the end effector. There is also a desire to lower the force necessary to articulate and/or actuate the working end to a level that all or a great majority of surgeons can handle. One known solution to lower the force-to-fire is to use electrical motors. However, surgeons typically prefer to experience feedback from the working end to assure proper operation of the end effector. The user-feedback effects are not suitably realizable in present motor-driven devices.

Accordingly, there remains a need for improved methods and devices for controlling movement of a working end of a surgical device.

BRIEF DESCRIPTION OF THE DRAWINGS

The invention will be more fully understood from the following detailed description taken in conjunction with the accompanying drawings, in which:

FIG. 1A is a perspective view of one embodiment of an insertion portion of a manually articulating device having an end effector with grasper jaws.

DESCRIPTION

Figure 1B:
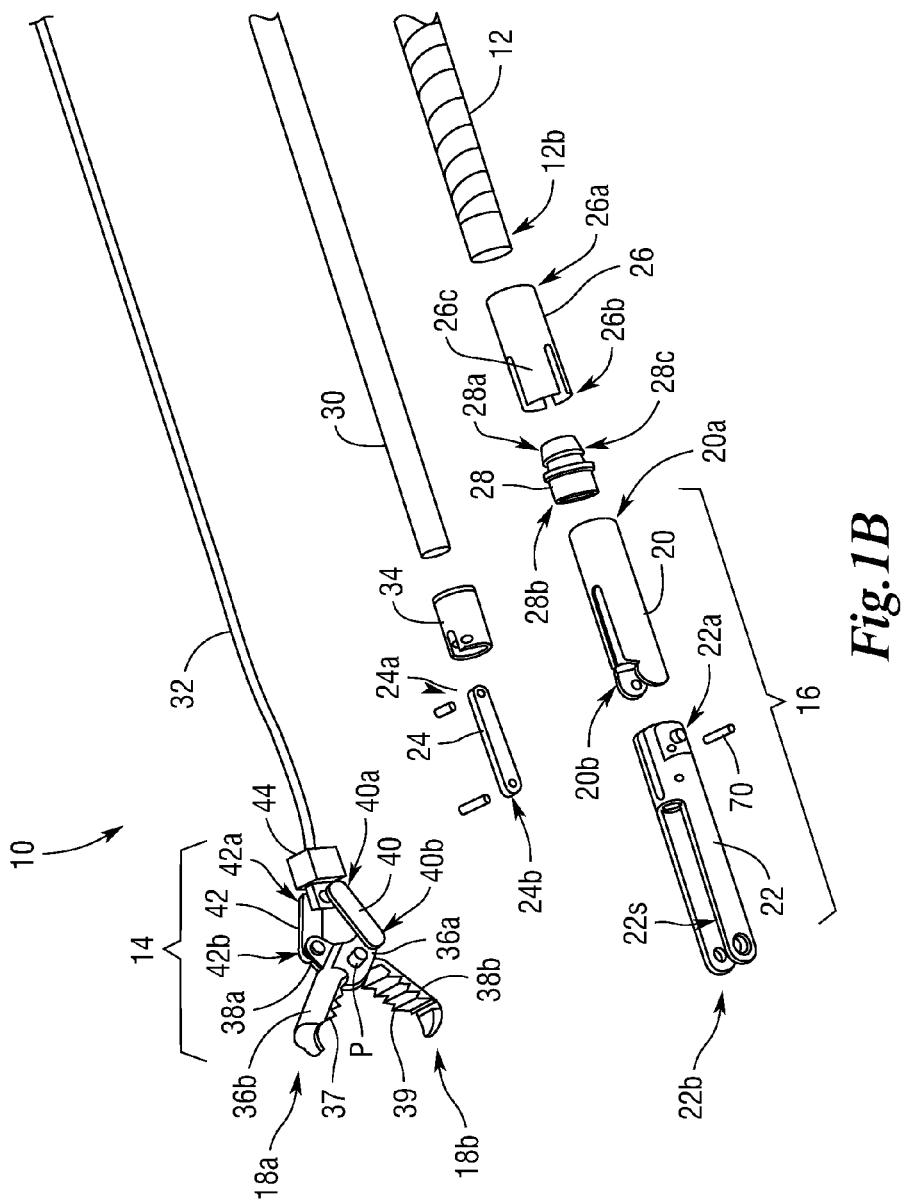
FIG. 1B is an exploded view of the insertion portion of the surgical device of FIG. 1A.

Methods and devices are provided for controlling the movement of a working end of a surgical device. In one embodiment a surgical device is provided having a flexible elongate shaft with a proximal and distal ends. The flexible elongate shaft is dimensioned to fit in the working channel of an endoscope. An articulating end may be coupled to the distal end of the flexible elongate shaft, having a straight position and an articulated position. An end effector may be coupled to the articulating end, the end effector is activated by an actuation wire. The articulating end articulates laterally relative to a longitudinal axis of the flexible elongate shaft about an articulation joint to allow the articulating end to be angularly oriented relative to the elongate shaft, wherein in the articulated position the actuation wire is at least partially aligned with the articulation joint.

In one embodiment, a surgical device is provided having an elongate shaft with proximal and distal ends. A proximal end of a three-bar linkage may be coupled to the distal end of the elongate shaft, and a distal end of the three-bar linkage is coupled to an end effector. The end effector can be, for example, a grasper, a biopsy probe, a snare loop, forceps, or scissors. In use, the three-bar linkage is adapted to laterally articulate relative to a longitudinal axis of the elongate shaft to allow the end effector to be angularly oriented relative to the elongate shaft. A decoupling member is utilized to isolate actuation of the end effector from articulation of the end effector. In other embodiments, other articulation configurations may be used.

The three-bar linkage of the device can have a variety of configurations, but in one embodiment the three-bar linkage includes a first articulating link having a proximal end coupled to the distal end of the elongate shaft, a second articulating link having a proximal end pivotally coupled to a distal end of the first articulating link and a distal end coupled to the end effector, and a third articulating link having a proximal end pivotally coupled to an articulation actuator extending through the elongate shaft and a distal end pivotally coupled to the second articulating link. In another embodiment, the third articulating link can be a flexible wire that is adapted to buckle when a force is applied thereto to cause the second articulating link to pivot relative to the first articulating link. In various embodiments, the second articulating link will have a decoupling member fixedly mated to or formed on its inner wall to route an actuating wire through the three-bar linkage. In various embodiments, the first articulating link will have a decoupling member fixedly mated to or formed on its inner wall.

The articulation actuator can also have a variety of configurations, but in one embodiment it is adapted to translate along a longitudinal axis of the elongate shaft to laterally articulate the second link and the end effector relative to the first link. In one embodiment, the articulation actuator is in the form of a hollow elongate tube. The articulation actuator also can be rotatable relative to the elongate shaft such that rotation of the articulation actuator rotates the three-bar linkage and the end effector relative to the elongate shaft. In other embodiments, the device can include an actuation wire extending through the elongate shaft and the three-bar linkage and adapted to translate along a longitudinal axis of the elongate shaft to actuate the end effector. The decoupling member serves to direct the path of the actuation wire through the three-bar linkage and isolate the actuation of the end effector from the articulation of the end effector. The elongate shaft of the device can also optionally be flexible to allow the shaft to be inserted through a tortuous lumen.

Certain embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting embodiments and that their scope is defined solely by the claims. The features illustrated or described in connection with one embodiment may be combined with the features of other embodiments. Such modifications and variations are intended to be included within the scope of the present invention.

The various embodiments generally provide methods and devices for controlling the movement of a working end of a surgical device, and in particular for performing various surgical procedures using an instrument having an end effector that can be articulated (or angularly oriented) relative to an elongate shaft of the device and actuated (i.e., fired, opened and closed, energized, etc.). In certain embodiments, the end effector can also optionally rotate relative to the elongate shaft of the device, and/or the shaft can rotate relative to a handle of the device. Articulation and rotation of the end effector will allow the end effector to be positioned at various locations during a surgical procedure, thereby providing the user with precise control over the end effector. The actuation of the end effector is isolated from the articulation of the end effector so that actuation of the end effector will not cause angular rotation of the end effector about its articulating joint. A person skilled in the art will appreciate that the present invention has applications in endoscopic procedures, laparoscopic procedures, and in conventional open surgical procedures, including robotic-assisted surgery.

It will be appreciated that the terms "proximal" and "distal" are used herein with reference to a clinician manipulating one end of an instrument that protrudes out of a natural orifice (or opening) of the patient. The term "proximal" refers to the portion of the instrument closest to the clinician and the term "distal" refers to the portion located furthest from the clinician. It will be further appreciated that for conciseness and clarity, spatial terms such as "vertical," g"horizontal," g"up," and "down" may be used herein with respect to the drawings. However, surgical instruments may be used in many orientations and positions, and these terms are not intended to be limiting and absolute.

FIGS. 1A and 1B illustrate one embodiment of an insertion portion 10 of a manually articulating device. A handle portion of the device will be discussed in more detail below with respect to FIGS. 4A-4D. The insertion portion 10 is preferably configured to be inserted into a patient's body, and it can be rigid for laparoscopic applications, flexible for endoscopic applications, or it can have rigid and flexible portions as may be desired. As shown, the insertion portion 10 generally includes a hollow elongate shaft 12 having a working end or end effector 14 coupled to a distal end 12b thereof by a three-bar linkage 16. While the end effector 14 can have various configurations, as will be discussed in more detail below, in the illustrated embodiment the end effector 14 is in the form of graspers having opposed jaws 18a, 18b that are pivotally coupled to one another. The three-bar linkage 16 allows the end effector 14 to be oriented at an angle relative to a longitudinal axis L of the elongate shaft 12. The device optionally can be configured to allow the end effector 14 to rotate relative to and about the longitudinal axis L of the elongate shaft 12. In the illustrated embodiment, the three-bar linkage 16 is rotatably coupled to the distal end 12b of the elongate shaft 12, and thus the three-bar linkage 16, as well as the end effector 14 coupled thereto, can be positioned in various axial orientations. The location of the rotation joint R proximal of the articulation joint A is particularly advantageous in that rotation of the end effector 14 can change the location of the plane within which the end effector 14 articulates.

Figure 1C:
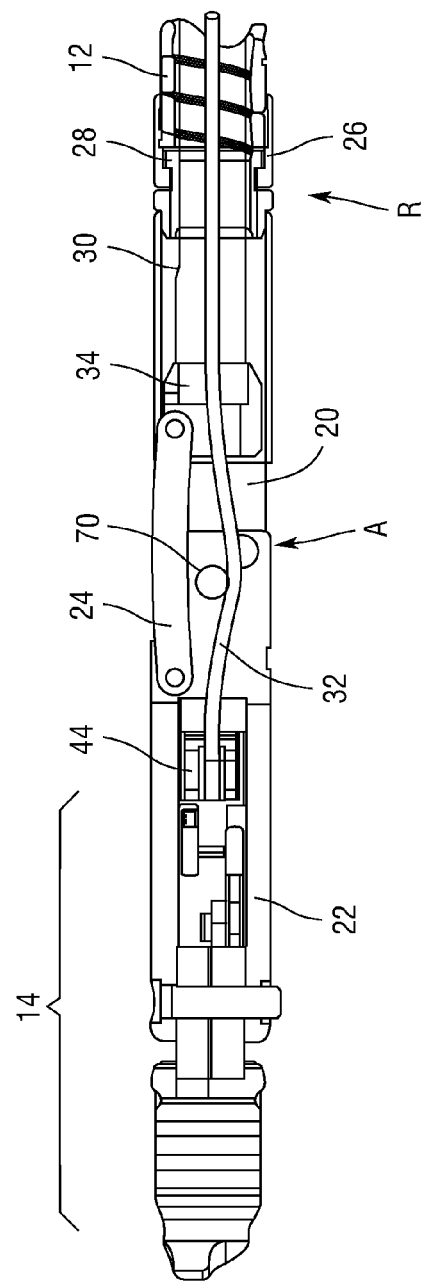
FIG. 1C is a cross-sectional view of one embodiment showing a three-bar linkage in a non-articulated position.
Figure 1D:
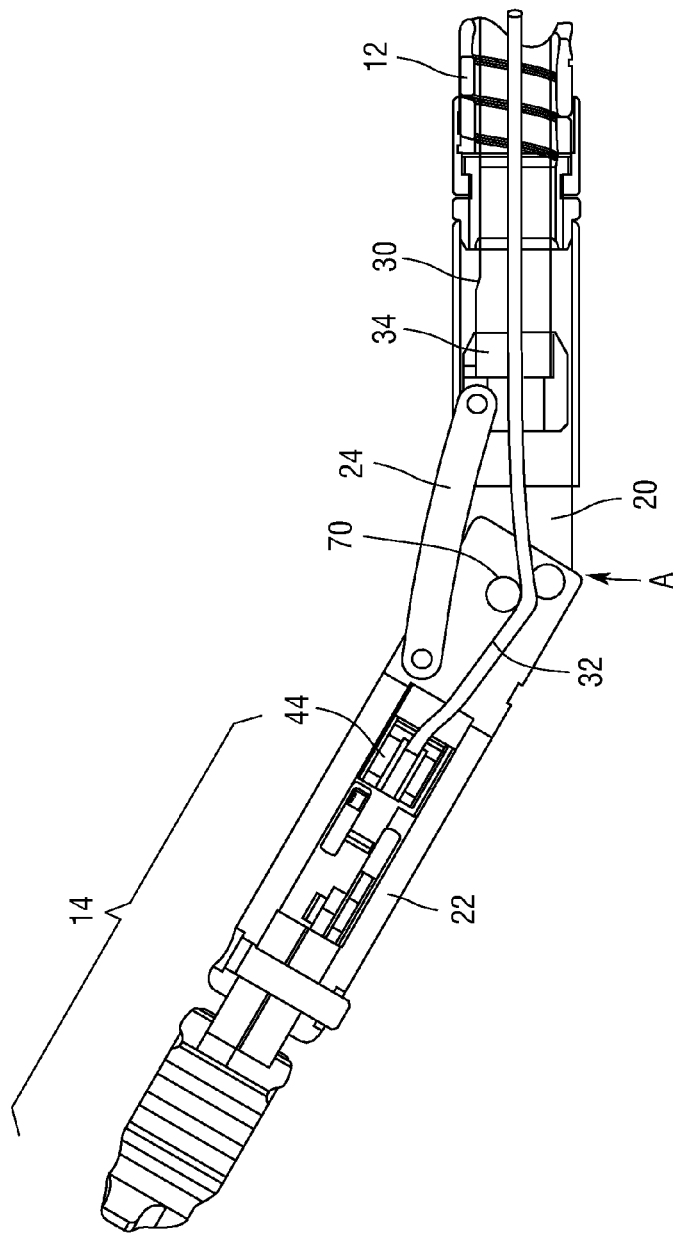
FIG. 1D is a cross-sectional view of one embodiment showing a three-bar linkage articulated to position an end effector of the device at an angle relative to an elongate shaft of the device.

The three-bar linkage 16 can have a variety of configurations, but in an embodiment, as shown in more detail in FIGS. 1B-1D, it includes three links 20, 22, 24 that are pivotally coupled to one another. Each link can have a variety of configurations, but in one embodiment the first and second links 20, 22 each have a generally hollow elongate shape and the third link 24 is in the form of an elongate rod or bar. The first link 20 can have a proximal end 20a that is coupled to a distal end 12b of the elongate shaft 12 via first and second rotation couplings 26, 28, which will be discussed in more detail below. The distal end 20b of the first link 20 can be pivotally coupled to a proximal end 22a of the second link 22, e.g., by a pivot joint. The distal end 22b of the second link 22 can in turn be coupled to the end effector 14, which will be discussed in more detail below. The third link 24 can extend at least partially through the first and second links 20, 22, and it can have a distal end 24b that is pivotally coupled to the second link 22, e.g., by a pivot pin, to form a three-bar linkage mechanism. The particular location at which the third link 24 mates to the second link 22 can vary, but it is preferably pivotally mated at a location that will allow the third link 24 to apply a force to the second link 22 to cause the second link 22 to articulate relative to the first link 20. The proximal end of the third link 24 can be coupled to an articulation actuator 30 extending through the elongate shaft 12 and at least partially through the first link 20. The articulation actuator 30 can have a variety of configurations, but in one embodiment the articulation actuator 30 is in the form of a hollow elongate shaft or tube. Such a configuration allows an actuation wire 32 to extend therethrough for actuating the end effector 14, as will be discussed below. FIG. 1B also illustrates an articulation coupling 34 for connecting the articulation actuator 30 to the third link 24. The coupling 34 is merely a tubular member that fixedly mates to the articulation actuator 30 and pivotally mates to the third link 24. A person skilled in the art will appreciate that the articulation actuator 30 can be directly mated to the third link 24.

Figure 1E:
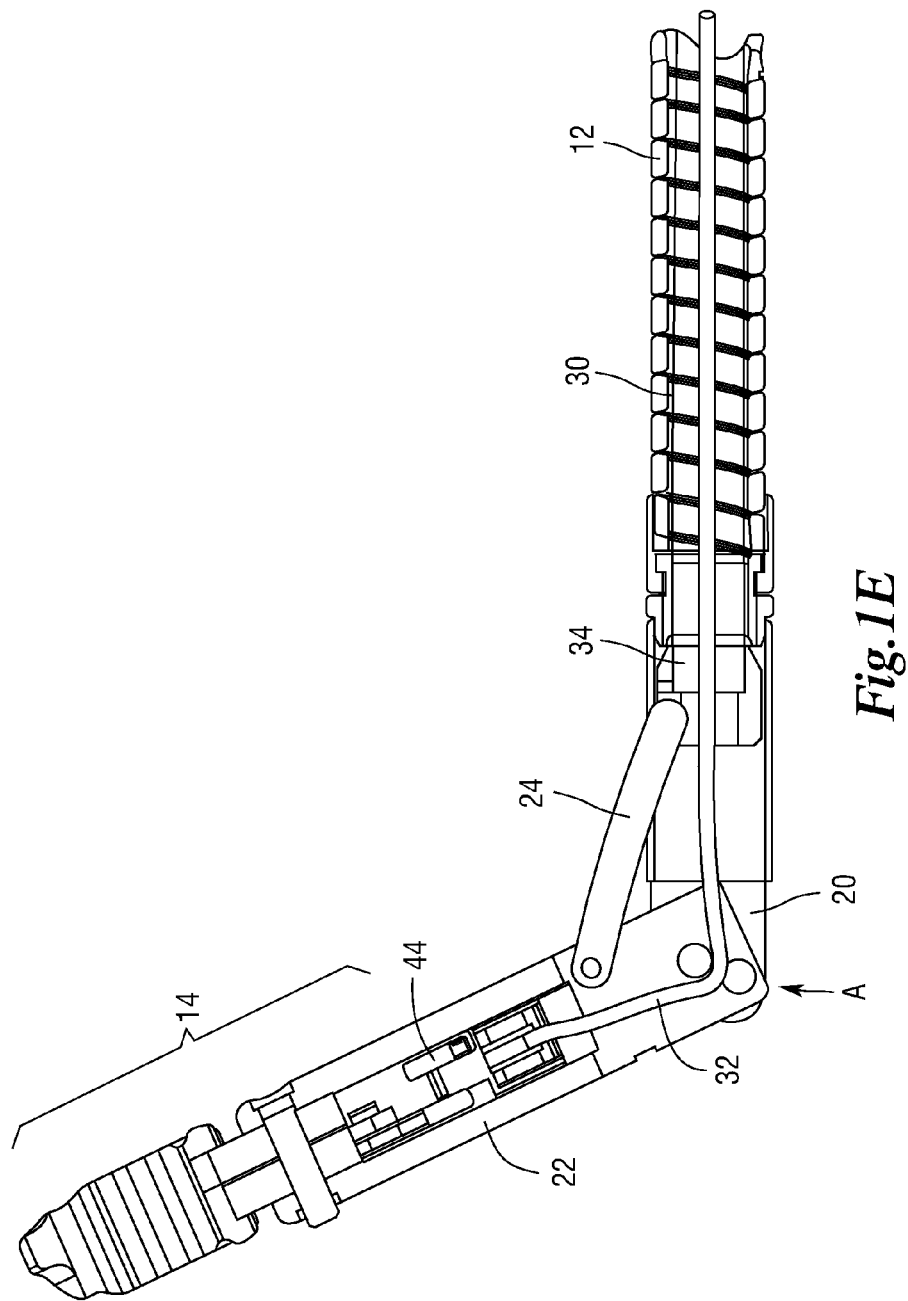
FIG. 1E is a cross-sectional view of one embodiment showing a three-bar linkage articulated to position an end effector of the device at an angle relative to an elongate shaft of the device.

In use, proximal movement of the articulation actuator 30 relative to and along the longitudinal axis L of the elongate shaft 12 will apply a proximally-directed force to the third link 24. The third link 24 will thus apply a proximally-directed force to the second link 22, causing the second link 22 to pivot laterally relative to the longitudinal axis L of the elongate shaft 12. As a result, the second link 22, with the end effector 14 coupled thereto, will move laterally in a single plane to allow the end effector 14 to extend at an angle relative to the longitudinal axis L of the elongate shaft 12, as shown in FIGS. 1D-1E. The end effector 14 can be returned to the original, longitudinally-aligned position, shown in FIGS. 1A and 1C, by moving the articulation actuator 30 distally relative to the elongate shaft 12.

As previously indicated, in addition to articulating movement, the end effector 14 can be configured to rotate relative to the elongate shaft 12, thus allowing the end effector 14 to be positioned in multiple angular orientations. The particular location of the rotation joint R can vary, and it can be located proximal to the three-bar linkage 16, at a mid-portion of the three-bar linkage 16, or distal to the three-bar linkage 16. In one embodiment, the rotation joint R is located proximal to the three-bar linkage 16, and more preferably proximal to the articulation joint A formed between the first and second links 20, 22. As shown in FIGS. 1A-1B, the first link 20 can be rotatably coupled to the distal end 12b of the elongate shaft 12 by one or more rotation couplings. The illustrated embodiment includes first and second rotation couplings 26, 28. The first rotation coupling 26 has a generally elongate hollow shape with a proximal end 26a that is fixedly mated to the elongate shaft 12 and a distal end 26b having deflectable tabs 26c formed therearound. The tabs 26c can be formed by longitudinally-extending cutouts formed in and spaced radially around the distal end 26b of the first rotation coupling 26. Each tab 26c can include an annular flange or lip (not shown) formed on an inner surface thereof. The second rotation coupling 28 can also have a generally elongate hollow shape, and it can include a groove or cutout 28c formed therein. The first and second rotation couplings 26, 28 can be mated by advancing the tabs 26c over the proximal end 28a of the second rotation coupling 28. The tabs 26c will deflect until the annular flange or lip on the tabs 26c extends into and engages the groove 28c formed in the second rotation coupling 28. The two rotation couplings 26, 28 can thus rotate relative to one another, allowing the first link 20, which is fixedly mated to the distal end 28b of the second rotation coupling 28, to rotate relative to the first rotation coupling 26 and the elongate shaft 12.

Rotation of the articulation actuator 30 can be achieved by rotating the articulation actuator 30. In particular, rotation of articulation actuator 30 relative to and about the longitudinal axis L of the elongate shaft 12 will rotate the third link 24, which is coupled to the second link 22, which in turn is coupled to the end effector 14 and the first link 20. As a result, the entire three-bar linkage 16 will rotate with the end effector 14 relative to and about the longitudinal axis L of the elongate shaft 12. Rotation can also be done while the end effector 14 is articulated, thereby changing the plane within which the end effector 14 articulates.

Still referring to the embodiment of FIGS. 1A-1E, the end effector 14 of the device can have various configurations but in the embodiment shown in FIGS. 1A and 1B the end effector 14 is in the form of a grasper having opposed jaws 18a, 18b. As best shown in FIG. 1B, each jaw 18a, 18b includes a distal portion 36b, 38b having a series of teeth 37, 39 formed thereon for grasping tissue, and a proximal portion 36a, 38a that pivotally mates to a distal end 40b, 42b of an actuation link 40, 42. The jaws 18a, 18b are pivotally mated to one another at a pivot point P located between the proximal and distal portions 36a, 38a, 36b, 38b. The distal end 24b of the second link 24 is also mated to the opposed jaws 18a, 18b at the pivot point P. The proximal end 40a, 42a of each actuation link 40, 42 is pivotally mated to an actuation pusher 44. The particular configuration of the actuation pusher 44 can vary, but in one embodiment the actuation pusher 44 has a generally rectangular configuration and is slidably disposed within and between opposed slots 22s formed in a distal portion of the second link 22. Such a configuration will prevent independent rotation of the actuation pusher 44 relative to the second link 22. The actuation wire 32 can have a variety of configurations, but in one embodiment it is an elongate flexible cable or wire that extends through second link 22, the articulating coupling 34 which is disposed within the first link 20, and the articulation actuator 30. Actuation wire 32 may be constructed from any suitable material. First example, in various embodiments actuation wire 32 may be metal, non-metal, fiberous, cable, braided, coated, coiled, round, or non-round.

Three-bar linkage 16 includes a decoupling member 70. As shown in FIGS. 1B-1E, the second link 22 may be configured with the decoupling member 70. The decoupling member 70 can be fixedly mated to or formed on an inner wall of the second link 22. The second link 22 may have opposed bores spaced to receive the decoupling member 70. The decoupling member 70 can have a variety of configurations. For instance, the decoupling member 70 may be axially rotatable using a roller pin, a bearing, or other suitable configuration. In various embodiments the decoupling member 70 may be lubricated to lower the coefficient of friction between decoupling member and the actuation wire 32. As illustrated, the decoupling member 70 may be located in the proximal end 22a of the second link 22 in an orientation parallel to the articulation joint. In other configurations, the decoupling member 70 may be mated to or formed on an inner wall of the first link 20. Some configurations may have multiple decoupling members, for instance, the decoupling member 70 may be mated to or formed on inner walls of both the first and second links 20, 22.

As actuation wire 32 extends through the second link 22 and the first link 20 its path is diverted by the decoupling member 70. The decoupling member 70 routes the actuation wire 32 in a path that is directed generally toward the articulation joint. As discussed in more detail below, by altering the path of the actuation wire 32, actuation (i.e., for firing, opening and closing, energizing, etc,) of the end effector 14 will not tend to affect the articulation (or hinging) of the end effector 14. The decoupling member 70 serves to isolate the actuation of the end effector 14 from the articulation of the end effector 14.

In use, proximal movement of the actuation wire 32 relative to the elongate shaft 12 will pull the actuation pusher 44 proximally within the slots 22s formed in the second link 22. The actuation links 40, 42 will thus be pulled proximally, bringing the proximal and distal portions 36a, 38a, 36b, 38b of each of the jaws 18a, 18b toward one another to thereby close the jaws 18a, 18b. Conversely, distal movement of the actuation wire 32 within the slots 22s formed in the second link 22 will move the actuation pusher 44 distally, which will cause the links 40, 42 and the proximal and distal portions 36a, 38a, 36b, 38b of the jaws 18a, 18b to pivot laterally outward, thereby opening the jaws 18a, 18b. The decoupling member 70 directs actuation wire 32 toward the pivot point of the end effector 14. By directing the actuation wire 32 toward the pivot point, any moment created about the articulation joint A during actuation of the end effector 14 is reduced. By reducing the moment, any tendency of the end effector 14 to change its articulation angle during actuation of the end effector 14 is reduced. Therefore, if the end effector 14 is in a non-articulated or longitudinally-aligned position, as the user moves the actuation wire 32 to open or close the jaws 18a, 18b, for example, the proximal movement of the actuation wire 32 will tend not to impart an articulating, or hinging-action upon the end effector 14. Conversely, if the end effector 14 is in an articulated or "hinged" position, as the user moves the actuation wire 32 to open or close the jaws 18a, 18b, for example, the proximal movement of the actuation wire 32 will tend not to affect the articulation of the end effector 14.

FIGS. 1C-1E are cross-sectional views of one embodiment illustrating the articulation progression. FIG. 1C shows the end effector 14 in a non-articulated or longitudinally-aligned position. The actuation wire 32 is directed toward the articulation joint A by the decoupling member 70. FIG. 1D shows the end effector 14 in a partially articulated position. As shown, the articulation coupling 34 has moved in the proximal direction. The actuation wire 32 is routed in a path proximate to the pivot point by way of the decoupling member 70. FIG. 1E shows the end effector 14 in a further articulated position. Due to the decoupling member 70, the actuation wire 32 is still routed in a path proximate to the articulation joint A in order to at least partially align the actuation wire 32 with the articulation joint A.

Figure 1F:
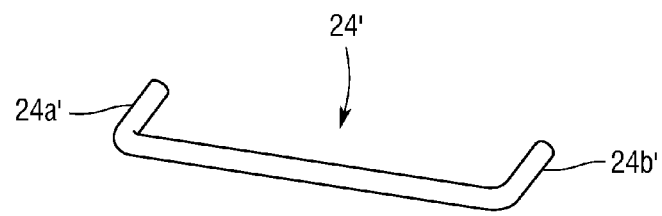
FIG. 1F is a perspective view of a link for use with a three-bar linkage in accordance with another embodiment.
Figure 1G:
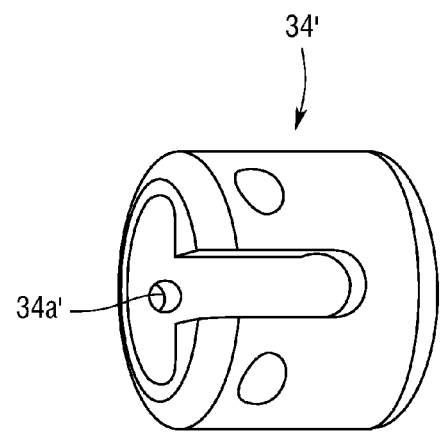
FIG. 1G is a perspective view of an articulating coupling configured for use with the link of FIG. 1F.

FIGS. 1F-1G illustrate alternative embodiments of a three-bar linkage. In one embodiment, shown in FIGS. 1F and 1G, the third link 24 of FIGS. 1B and 1D can be replaced with a flexible link. While the flexible link can have a variety of configurations, it can be in the form of a flexible cable or similar member, FIG. IF illustrates a flexible wire 24'. As shown, the wire 24' has a generally elongate shape with first and second terminal ends 24a', 24b' that are bent to extend at an angle, e.g., 90°, relative to the remainder of flexible wire 24'. The ends 24a', 24b' are configured to replace the pivot pins used to pivotally couple flexible wire 24' to the first and second links 20, 22 of the embodiment shown in FIGS. 1A-1E, thereby serving as a third link. Thus, the ends 24a', 24b' can extend into and pivotally couple to the first and second links 20, 22 (FIGS. 1B-1E) to allow the first, second, and third links 20, 22, 24' to pivot relative to one another. In use, proximal movement of the articulation actuator 30 relative to and along the longitudinal axis L of the elongate shaft 12 will apply a proximally-directed force to the third link 24'. The third link 24' will thus flex or buckle, thereby causing the second link 22 to pivot laterally relative to the longitudinal axis L of the elongate shaft 12. As a result, the second link 22, with the end effector 14 coupled thereto, will move laterally in a single plane to allow the end effector 14 to extend at an angle relative to the longitudinal axis L of the elongate shaft 12. The end effector 14 can be returned to the original, longitudinally-aligned position, shown in FIGS. 1A and 1C, by releasing the articulation actuator 30 to allow the flexible link 24' to return to its original, non-flexed position shown in FIG. 1F, thereby forcing the articulation actuator 30 to move distally relative to the elongate shaft 12. The flexible link 24' can also be used to transfer rotational forces to effect rotation of the end effector 14, but in one embodiment the articulating coupling 34 (FIGS. 1B-1E) is modified to be non-rotatably coupled to the first link 20. As shown in FIG. 1G, which illustrates an alternative embodiment of an articulating coupling 34', this can be achieved by inserting a pin member (not shown) through a bore 34a' formed in the articulating coupling 34', and positioning the pin member such that it is slidably disposed within a longitudinal slot (not shown) formed in the first link 20. As a result, when the articulation actuator 30 is rotated relative to and about the longitudinal axis L of the elongate shaft 12, the articulating coupling 34' will rotate therewith, thereby causing the first and second links 20, 22 to rotate, as well as the end effector 14. As a result, the entire three-bar linkage 16 will rotate with the end effector 14 relative to and about the longitudinal axis L of the elongate shaft 12. Rotation can also be done while the end effector 14 is articulated, thereby changing the plane within which the end effector 12 articulates.

Figure 2A:
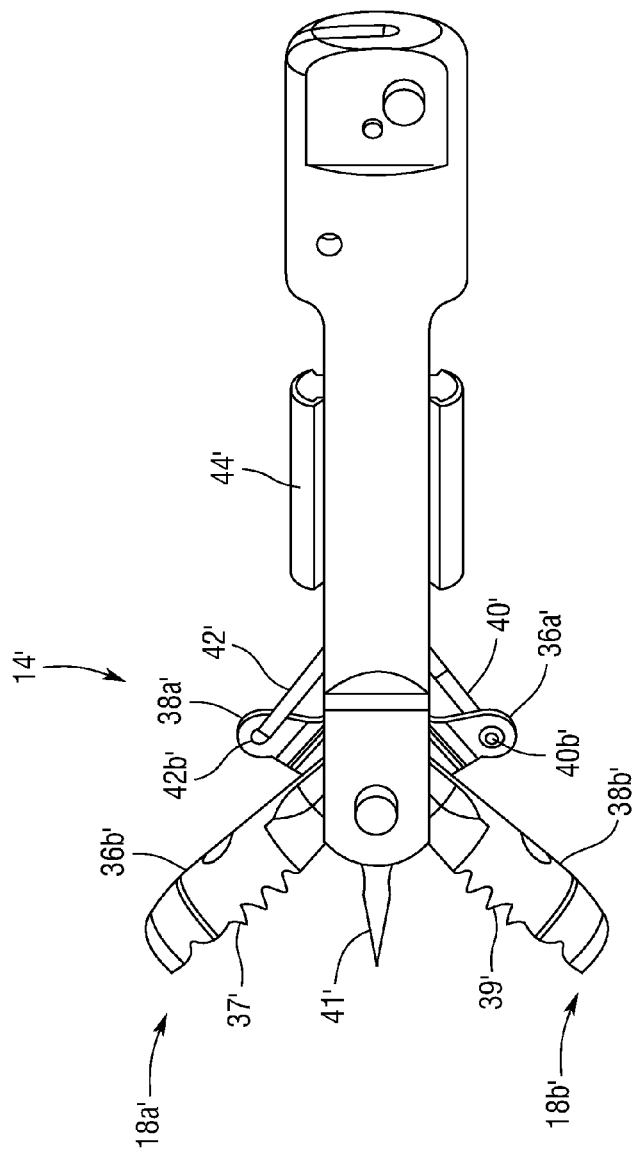
FIG. 2A is a perspective view of another embodiment of an end effector having opposed biopsy jaws and a spike for use with a manually articulating device.
Figure 2B:
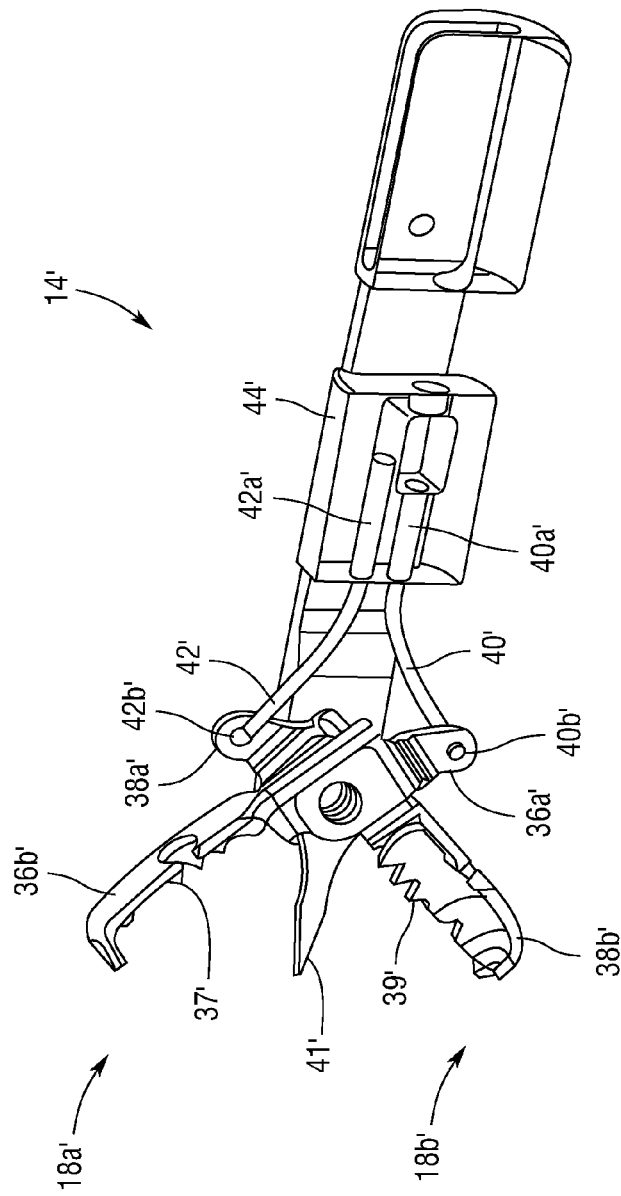
FIG. 2B is a cross-sectional view of the end effector of FIG. 2A.

FIGS. 2A and 2B illustrate an alternative embodiment of a mechanism for opening and closing opposed jaws. In this embodiment, the end effector 14' is in the form of biopsy jaws 18a', 18b'. The jaws 18a', 18b' are similar to the jaws 18a, 18b described above with respect to FIG. 1B; however, each of the jaws 18a', 18b' has a generally hollow configuration with teeth 37', 39' formed around a perimeter of the distal portions 36b', 38b' to allow the jaws 18a', 18b' to essentially bite off and remove a tissue sample. In this embodiment, the actuation links are replaced with pull wires 40', 42'. Each of the pull wires 40', 42' has a distal end 40b', 42b' that is coupled to the proximal portion 36a', 36b' of a jaw 18a', 18b', and a proximal end 40a', 42a' that is disposed within and fixedly coupled to the actuation pusher 44'. As with the previous embodiment, proximal movement of the actuation wire 32 and thus the actuation pusher 44' will pull the wires 40', 42' proximally to close the jaws 18a', 18b', and distal movement of the actuation wire 32 and thus the actuation pusher 44' will push the wires 40', 42' distally to open the jaws 18a', 18b'. A decoupling member (not shown) may be used to isolate the actuation of the jaws 18a, 18b from the articulation of the end effector 14'.

Figure 3A:
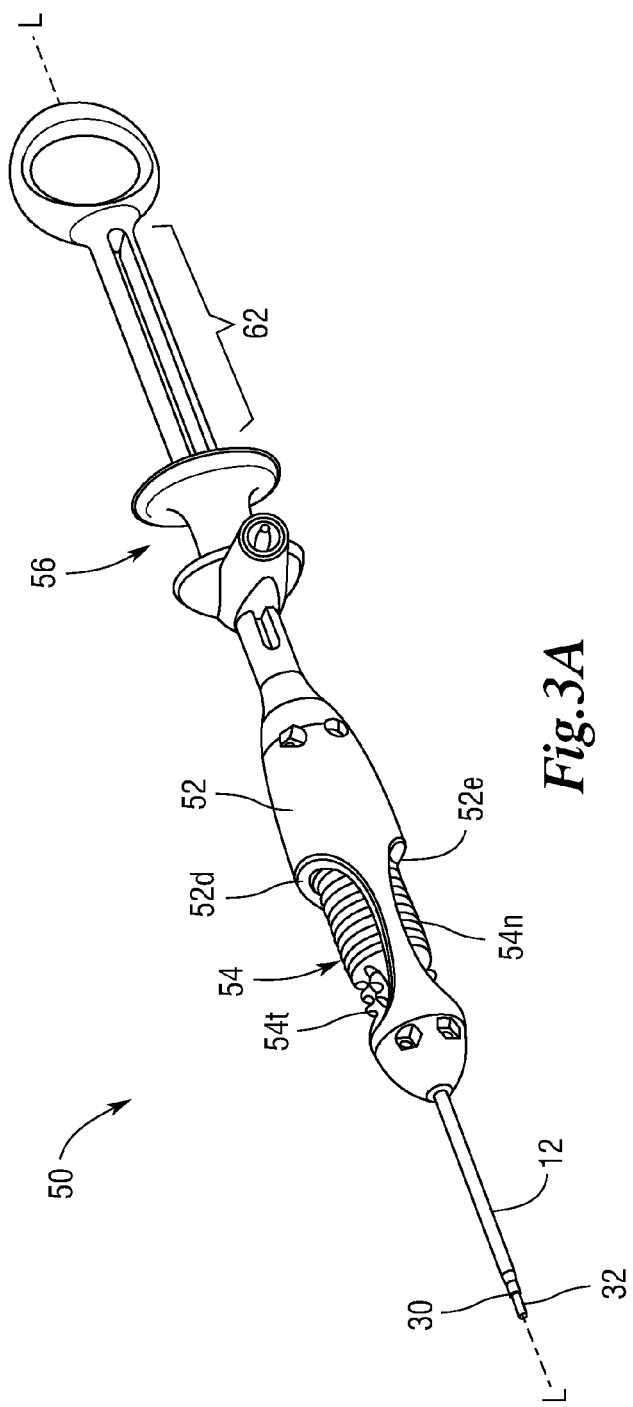
FIG. 3A is a perspective view of one embodiment of a handle portion of a manually articulating device.
Figure 3B:
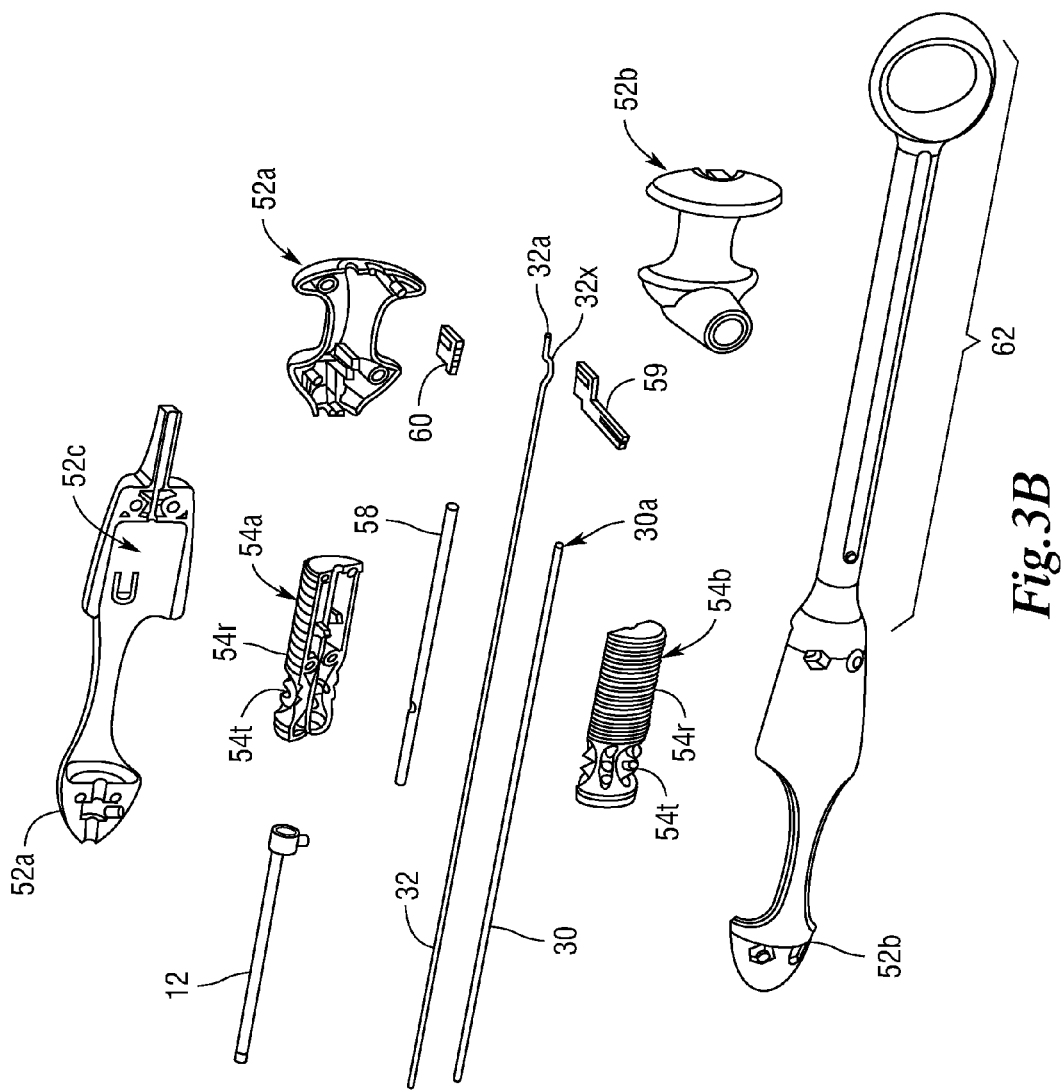
FIG. 3B is an exploded view of the handle portion shown in FIG. 3A.

As previously indicated, the device can include a handle coupled to the proximal end of the elongate shaft and having various controls formed thereon for controlling and manipulating the device. A person skilled in the art will appreciate that the particular configuration of the handle can vary, and that various techniques known in the art can be used for effecting movement of various portions on the device. FIGS. 3A-3D illustrate one embodiment of a handle 50 for use with the insertion portion 10 of the device shown in FIG. 1A. As shown, the handle 50 has a generally elongate cylindrical configuration to facilitate grasping thereof. The handle housing 52 can have an integral or unitary configuration, or it can be formed from two housing halves 52a, 52b that mate to enclose various components therein. The housing halves 52a, 52b are shown in FIG. 3B. The various components disposed within the handle housing 52 can also vary, but in one embodiment the handle 50 includes an articulation knob 54 for articulating and rotating the end effector 14, and an actuation knob 56 for actuating the end effector 14.

Figure 3C:
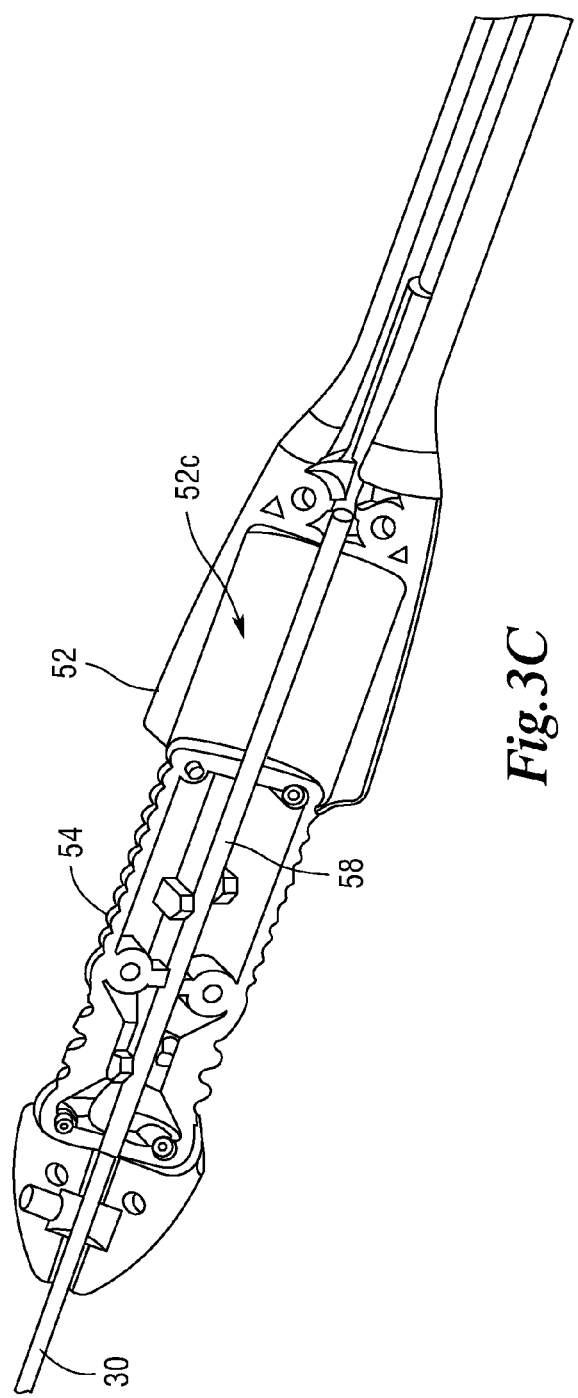
FIG. 3C is a cross-sectional view of the articulation mechanism of the handle portion shown in FIG. 3A.

The articulation knob 54 is shown in more detail in FIGS. 3B and 3C, and as shown the knob 54 has a generally cylindrical configuration. The knob 54 can have an integral or unitary configuration, or it can be formed from two halves 54a, 54b that mate together, as shown. The proximal end 30a of the articulation actuator 30 can mate to the knob 54 such that rotation and translation of the knob 54 will cause corresponding rotation and translation of the articulation actuator 30, thereby rotating and articulating the end effector 14, as previously described. While various techniques can be used to mate the articulation actuator 30 to the articulation knob 54, in one embodiment the articulation knob 54 includes an axle 58 fixedly disposed therein and engaged between the articulation knob halves 54a, 54b. The articulation actuator 30 extends through an inner lumen of the axle 58 and is fixedly mated thereto. Various mating techniques can be used to mate the articulation actuator 30 to the axle 58 including, for example, an interference or compression fit, an adhesive, or other mechanical or chemical mating techniques known in the art.

In order to translate and rotate the articulation knob 54, the handle housing 52 can include an elongate cavity 52c (FIG. 3B) formed therein that slidably and rotatably receives the articulation knob 54. The handle housing 52 may include one or more cutouts formed therein to allow a user to access the articulation knob 54. FIG. 3A illustrates opposed cutouts 52d, 52e formed in the handle housing 52. The articulation knob 54 may include features to facilitate movement thereof. For example, the articulation knob 54 can include one or more surface features formed on an external surface thereof to allow the user to more easily grasp the articulation knob 54. In the illustrated embodiment, the articulation knob 54 includes a series of ridges 54r formed therein, as well as a series of longitudinally-oriented teeth 54b formed on a portion thereof. The ridges 54r can provide a detent feature to maintain the position of the articulation. A corresponding detent snap can be located in the cavity 52c.

In use, the articulation knob 54 can be grasped by a user and rotated about its longitudinal axis (i.e., about the longitudinal axis L of the shaft 12 and the handle 50). Rotation of the articulation knob 54 will cause corresponding rotation of the axle 58 and the articulation actuator 30. The actuation wire 32, which extends through the articulation actuator 30, will not rotate with the articulation actuator 30 since it is not coupled thereto. As previously explained, rotation of the articulation actuator 30 will cause corresponding rotation of the three-bar linkage 16 and the end effector 14 coupled thereto. The articulation knob 54 can be slid or translated longitudinally along its axis L, and within the elongate cavity 52c formed in the handle housing 52. Proximal movement of the articulation knob 54 within the handle housing 52 will pull the articulation actuator 30 proximally, thereby articulating the end effector 14, as previously explained. Distal movement of the articulation knob 54 within the handle housing 52 will in turn move the articulation actuator 30 distally, thereby returning the end effector 14 to its original longitudinally-aligned position.

Figure 3D:
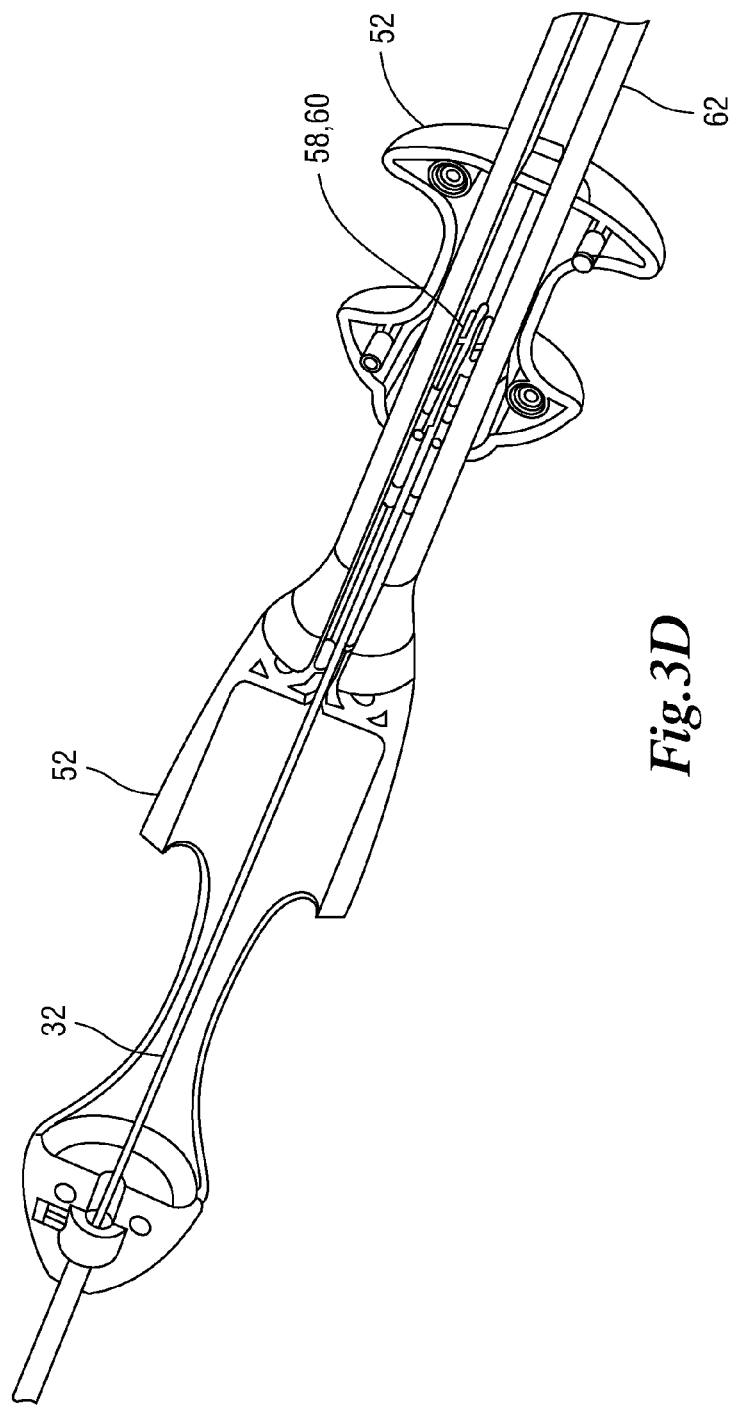
FIG. 3D is a cross-sectional view of an actuation mechanism of the handle portion shown in FIG. 3A.

As indicated above, the device may include an actuation knob 56 for actuating the end effector 14 (i.e. for firing, opening and closing, energizing, etc.). The actuation knob 56 can have a variety of configurations, but in the illustrated embodiment the actuation knob 56 has a barbell shape. The actuation knob 56 can have an integral or unitary configuration, or it can be formed from two halves 56a, 56b that mate together, as shown in FIG. 3B. The proximal end 32a of the actuation wire 32 can mate to the actuation knob 56 such that translation of the actuation knob 56 will cause corresponding translation of the actuation wire 32, thereby actuating the end effector 14, as previously described. While various techniques can be used to mate the actuation wire 32 to the actuation knob 56, in one embodiment the proximal end 32a of the actuation wire 32 includes a bend 32x formed therein for mating to the first and second retainer members 59, 60. The retainer members 59, 60, which engage the bend 32x in the wire 32 therebetween, can be disposed within and mated to the actuation knob 56, as shown in FIG. 3D.

In order to translate the actuation knob 56, the actuation knob 56 can include an inner lumen extending longitudinally therethrough and it can be slidably disposed around an elongate shaft portion 62 of the handle housing 52. In use, the actuation knob 56 can be grasped by a user and translated along the shaft portion 62 of the handle housing 52. Proximal movement of the actuation knob 56 along the shaft portion 62 will pull the actuation wire 32 proximally, thereby opening the jaws 18a, 18b of the end effector 14, as previously explained. Distal movement of the actuation knob 56 along the shaft portion 62 will in turn move the actuation wire 32 distally, thereby moving the jaws 18a, 18b to the closed position.

Figure 3E:
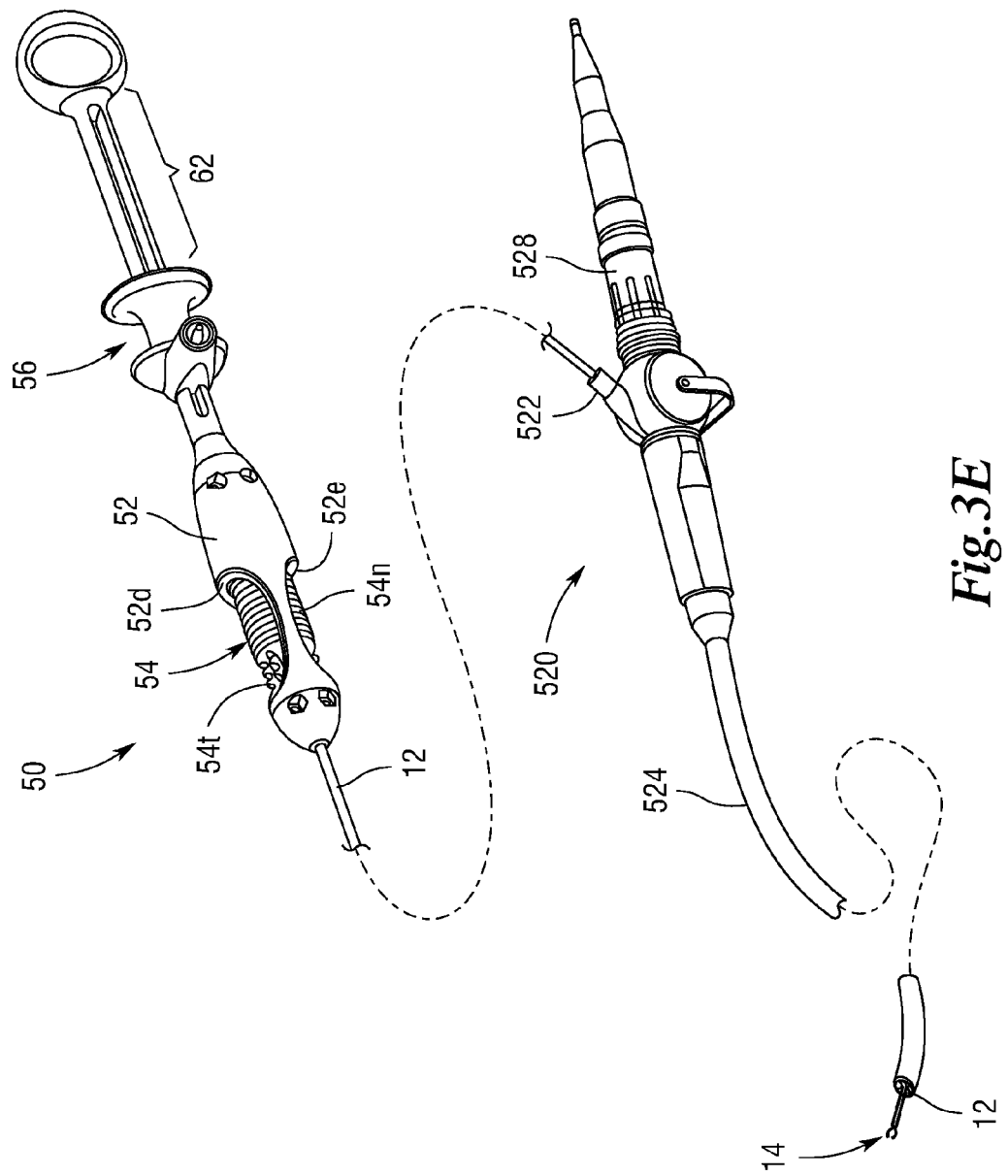
FIG. 3E illustrates one embodiment of the handle portion shown in FIG. 3A with an endoscope.
Figure 3F:
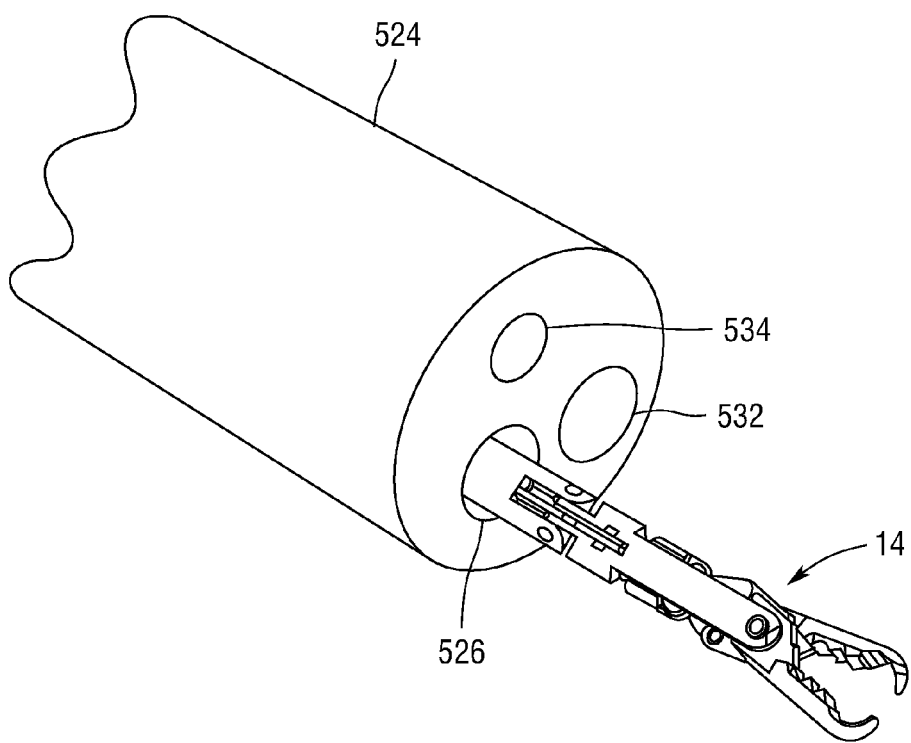
FIG. 3F illustrates an embodiment with an end effector protruding from the working channel of the endoscope shown in FIG. 3E.

FIG. 3E illustrates one embodiment using handle 50 with an endoscope 520. In various embodiments, other handles or devices used to control the end effector 14 may be used. In the illustrated embodiment, the elongate shaft 12 and end effector 14 are introduced into a port 522 in communication with a working channel of the endoscope 520. The end effector 14 protrudes from the distal end of a flexible endoscopic portion 124 of the endoscope 120. The endoscope 520 comprises a handle 528 and an elongated relatively flexible endoscopic portion 524. As shown in FIG. 3F, the distal end of the endoscopic portion 524 may comprise a light source 532, a viewing port 534, and a working channel 526. The viewing port 532 transmits an image within its field of view to an optical device such as a charge coupled device (CCD) camera within the endoscope 520 so that an operator may view the image on a display monitor (not shown).

In the illustrated embodiment, the flexible housing 12 is introduced through the port 522 coupled to the working channel 526 of the endoscope 520. The endoscope 520 comprises the flexible endoscopic portion 524 that is suitable to be inserted inside the patient through various natural orifices. In one embodiment, the endoscope 520 may be a GIF-100 model available from Olympus Corporation. The flexible endoscopic portion 524 of the endoscope 520 may be introduced into the patient trans-anally, trans-vaginally, orally, or through the abdomen via an incision or keyhole. The endoscope 520 assists the surgeon to guide and position the end effector 14 near the desired location.

Figure 4A:
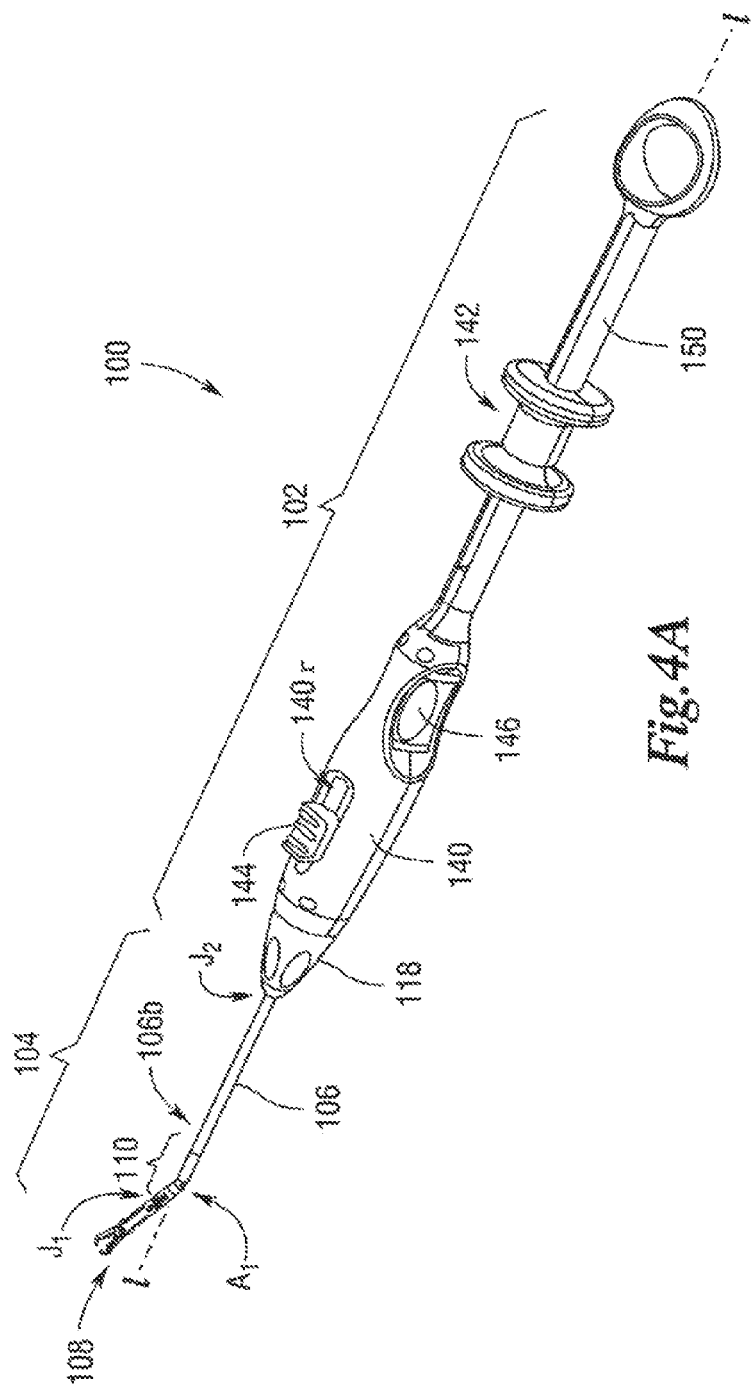
FIG. 4A is a perspective view of yet another embodiment of a manually articulating device having a handle portion and an insertion portion.

FIGS. 4A-4E illustrate another embodiment of a manually articulating device 100. The device is similar to the device shown in FIGS. 1A-1D and 4A-4D; however, in this embodiment the device 100 has one articulation joint $A_1$ and two rotation joints $J_1$, $J_2$. In general, the device 100 includes a handle portion 102 and an insertion portion 104 having an elongate shaft 106 with an end effector 108 coupled to a distal end 106b thereof by a three-bar linkage 110. As with the previous embodiment, the three-bar linkage 110 includes an articulation joint $A_1$ formed between the first and second links 112, 114 for laterally articulating the second link 114, with the end effector 108 coupled thereto, relative to the longitudinal axis l of the elongate shaft 106. As with the previous embodiment, the device 100 also can include a rotation joint $J_1$ configured to allow the end effector 108 to rotate relative to and about the longitudinal axis l of the elongate shaft 108. As with the previous embodiment, the three-bar linkage 110 includes a decoupling member 170. In this embodiment, however, the rotation joint $J_1$ is located distal of the articulation joint $A_1$. As a result, the end effector 108 can rotate relative to the three-bar linkage 110. The location of the rotation joint $J_1$ distal to the articulation joint $A_1$ is particularly advantageous in that it allows the axial position of the end effector 108 to be oriented as desired after the end effector 108 has been articulated to a desired angle. The device 100 also can include the second rotation joint $J_2$. As shown in FIG. 4A, the elongate shaft 106 is rotatably coupled to a rotation knob 118 formed on the distal end of the handle 102. Thus, the entire shaft 106, as well as the three-bar linkage 110 and the end effector 108 coupled thereto, can rotate relative to the handle 102. The location of the second rotation joint $J_2$ proximal to the articulation joint $A_1$ is particularly advantageous in that rotation of the end effector 108 can change the location of the plane within which the end effector 108 articulates.

Figure 4B:
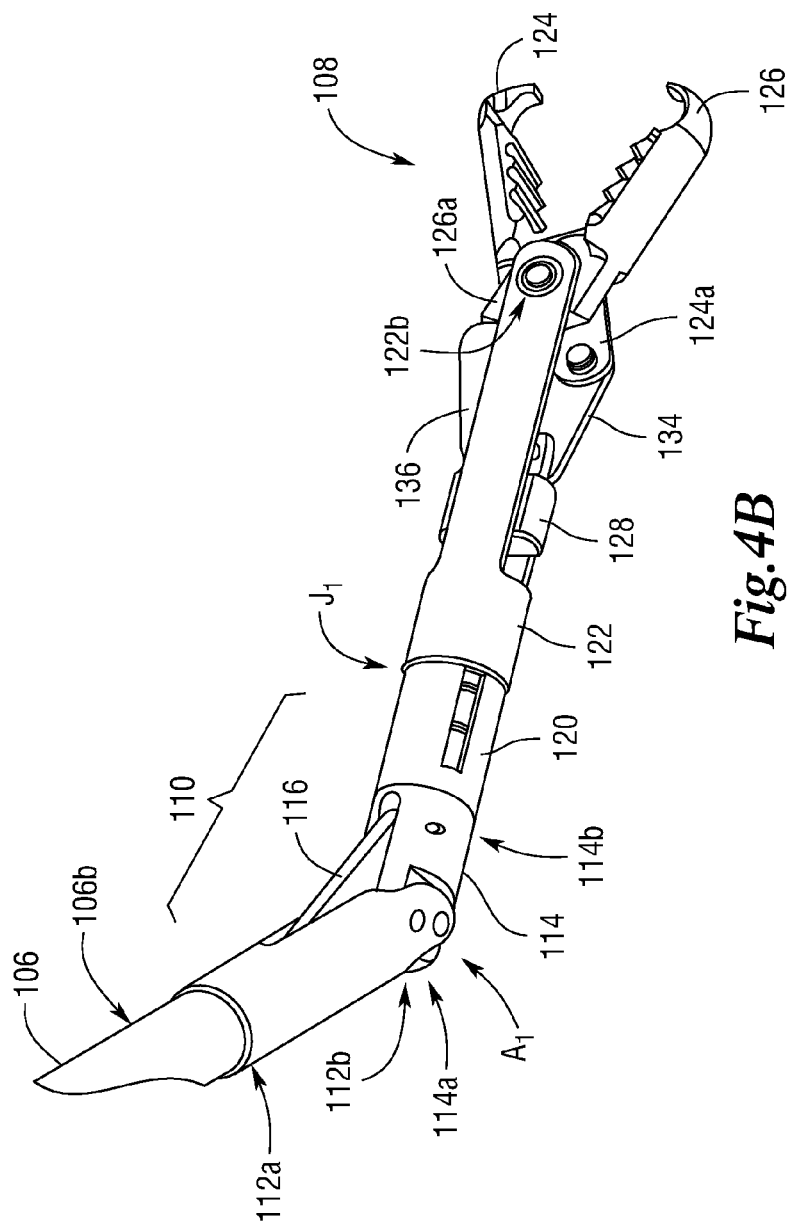
FIG. 4B is a perspective view of a distal end of the insertion portion of the device of FIG. 4A.
Figure 4C:
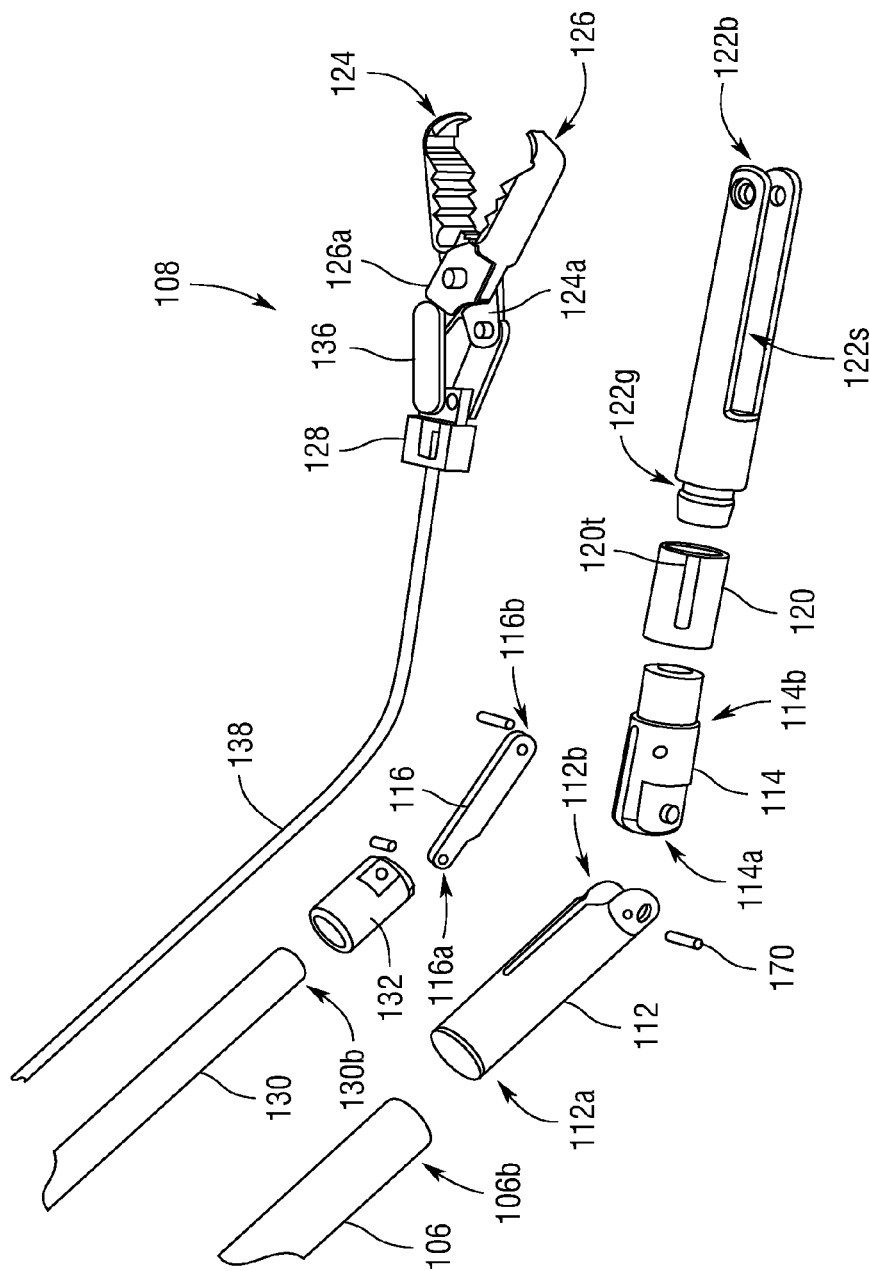
FIG. 4C is an exploded view of the insertion portion shown in FIG. 4B.

FIGS. 4B and 4C illustrate the three-bar linkage 110, i.e., the articulation joint $A_1$ and the first rotation joint $J_1$, in more detail. As shown, the three-bar linkage 110 is similar to the three-bar linkage previously described and generally includes first, second, and third links 112, 114, 116. In this embodiment, the first link 112 has a proximal end 112a that is fixedly mated to the distal end 106b of the elongate shaft 106, and a distal end 112b that is pivotally mated to a proximal end 114a of the second link 114. The distal end 112b further comprises a decoupling member 170. The distal end 114b of the second link 114 is coupled to the end effector 108 via a rotation coupling 120. Thus, unlike the previous embodiment where the distal end of the second link mated directly to the opposed jaws of the end effector, here the distal end 1 14b mates to a rotation coupling 120, which in turn mates to a clevis 122 that is mated to opposed jaws 124, 126 of the end effector 108. The rotation coupling 120 is similar to the rotation coupling 26 previously discussed, and generally includes flexible tabs 120t formed on the distal end thereof and having an annular flange or lip (not shown) formed on an inner surface thereof. The clevis 122 can have a generally elongate tubular configuration for receiving an actuation pusher 128 of the end effector 108 therein, as with the previous embodiment, and it can include a groove 122g formed in the proximal end thereof for receiving the annular lip formed in the rotation coupling 120. As a result, the rotation coupling 120 and the clevis 122 will rotatably mate relative to one another, thereby allowing the second link 114 to rotate relative to the clevis 122 and thus the end effector 108. As with the three-bar linkage 16 previously described, the second link 114 is pivotally mated to a distal end 116b of the third link 116, and a proximal end 116a of the third link 116 mates to the articulation actuator 130. An articulation coupling 132 is shown for mating the third link 116 to the articulation actuator 130; however, the third link 116 can optionally be directly mated to the distal end 130b of the articulation actuator 130.

FIGS. 4B and 4C also illustrate the end effector 108 that has a configuration similar to the end effector 14 previously described. In particular, the end effector 108 generally includes first and second jaws 124, 126 pivotally coupled to one another and to a distal end 122b of the clevis 122. First and second actuation links 134, 136 are pivotally coupled to a proximal portion 124a, 126a of the first and second jaws 124, 126, and an actuation pusher 128 is pivotally coupled to the first and second actuation links 134, 136. The actuation pusher 128 is slidably disposed within and extends between two opposed slots 122s formed in the clevis 122. An actuation wire 138 is coupled to the actuation pusher 128, and it is effective to translate axially relative to the articulation actuator 130 and the elongate shaft 106 to move the jaws 124, 126 between the open and closed positions. In this embodiment, the actuation wire 138 is also rotatable relative to the elongate shaft 106 and the articulation actuator 130. Rotation of the actuation wire 138 will cause the actuation pusher 128 to rotate, thereby causing the clevis 122 and the remainder of the end effector 108 to rotate relative to the rotation coupling 120. As with previous embodiments, the decoupling member 170 may be used to isolate the actuation of the jaws 124, 126 from the articulation of the end effector 108. As shown in this embodiment, the decoupling member 170 may be fixedly mated to or formed on an inner wall of the first link 112 in order to direct the path of the actuation wire 138 toward the articulation joint A of the first link 112 and the second link 114.

Figure 4D:
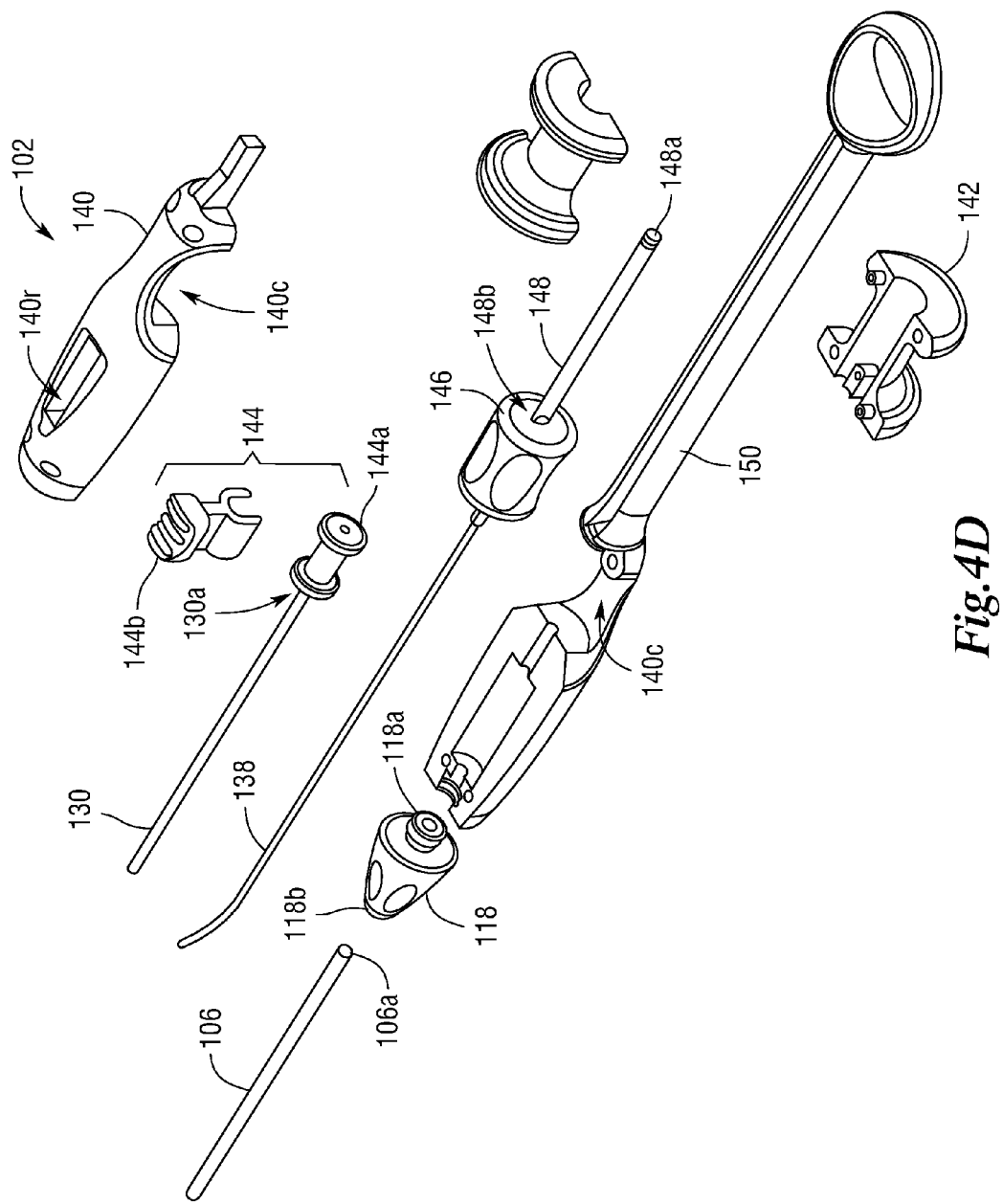
FIG. 4D is an exploded view of the handle portion of the device of FIG. 4A.
Figure 4E:
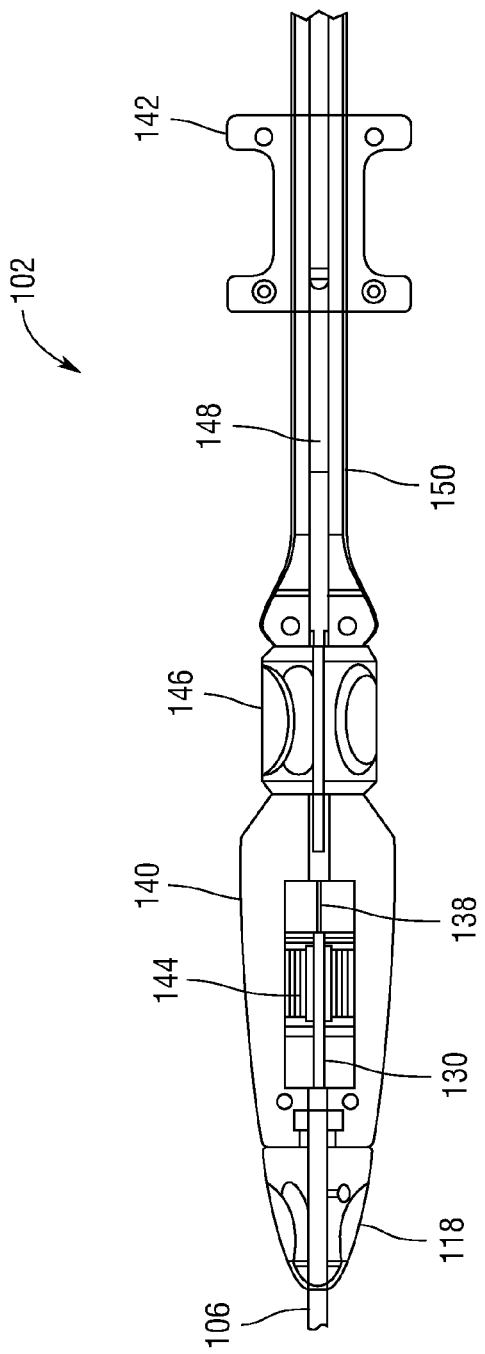
FIG. 4E is a cross-sectional view of the handle portion shown in FIG. 4A.

Referring back to FIG. 4A, the handle 102 can include certain features similar to the handle 50 previously described, including a handle housing 140 and an actuation knob 142. In this embodiment, the articulation knob 54 previously described with respect to FIGS. 3A-3C is replaced by two knobs: an articulation lever 144 and a rotation knob 146. The articulation lever 144 is slidably disposed within a cutout 140r formed in the handle housing 140, and it is coupled to the proximal end of the articulation actuator 130. FIGS. 4D-4E illustrate the handle 102 of the device 110 in more detail. While the articulation lever 144 can have a variety of configurations, in the illustrated embodiment the articulation lever 144 includes an articulation spool 144a that is fixedly mated to the proximal end 130a of the articulation actuator 130, and a button 144b that engages the spool 144a and that is adapted to be grasped by a user. In use, the button 144b extends through the cutout 140r formed in the handle housing 140, thus allowing a user to grasp the button 144b and slide the lever 144 proximally and distally. Proximal movement of the articulation lever 144 will pull the articulation actuator 130 proximally, thereby causing the three-bar linkage 110 to articulate to position the end effector 108 at an angle relative to the longitudinal axis l of the elongate shaft 106, as previously described. Likewise, distal movement of the articulation lever 144 will return the three-bar linkage 110 to a longitudinally aligned position, thereby returning the end effector 108 to the longitudinally aligned position.

As indicated above, the handle 102 may include a rotation knob 146 disposed therein. The rotation knob 146 can have a variety of configurations, but in one embodiment it is adapted to rotate axially relative to the handle housing 140 to rotate the actuation wire 138, and thereby rotate the end effector 108 relative to the second link 114. In the embodiment shown in FIGS. 4D and 4E, the rotation knob 146 is in the form of a generally cylindrical member that is rotatably disposed within a cylindrical cavity 140c formed in the handle housing 140. The rotation knob 146 can include surface features, such as detents, formed thereon to facilitate grasping of the rotation knob 146. As further shown, the rotation knob 146 is disposed around a portion of an actuation spool 148. While not shown, the actuation spool 148 can be slidably but non-rotatably coupled to the rotation knob 146. This can be achieved by forming at least a portion of the spool 148 to have an asymmetrical shape that slidably and non-rotatably mates with an asymmetrical lumen extending through the actuation spool 148. Such a configuration allows the spool 148 to rotate with the rotation knob 146 and to translate with the actuation knob 142, as discussed below. As further shown, a distal end 148b of the actuation spool 148 is fixedly mated to a proximal end of the actuation wire 138 such that rotation of the rotation knob 146 will rotate the spool 148 and thus the actuation wire 138. The proximal end 148a of the actuation spool 148 is rotatably coupled to the actuation knob 142. The rotatable connection allows the actuation spool 148 to rotate with the rotation knob 146, while allowing the actuation knob 142 to remain in a fixed axial position. As with the previous embodiment, the actuation knob 142 is effective to translate along an elongate shaft portion 150 of the handle housing 140 to move the actuation wire 138 proximally and distally, thereby actuating the end effector 108, e.g., opening and closing the jaws 124, 126. In this embodiment, the actuation knob 142 will pull the actuation spool 148, and thus the actuation wire 138 coupled thereto, proximally and distally relative to the handle housing 140. A person skilled in the art will appreciate that a single knob or lever can be used to effect both translation and rotation of the actuation wire, and that a variety of other techniques in the art can be used instead of those shown in FIGS. 4D-4E.

As further shown in FIGS. 4D and 4E, the handle 102 also includes a second rotation knob 118 coupled to a distal end of the handle housing 140. The second rotation knob 118 can have various configurations, but in the illustrated embodiment it has a generally cylindrical or conical configuration with surface features formed therearound to facilitate grasping. The second rotation knob 118 has a proximal end 118a that is rotatably coupled to the handle housing 140, and a distal end 118b that is fixedly mated to the proximal end 106a of the elongate shaft 106. In use, rotation of the second rotation knob 118 will rotate the elongate shaft 106 and thus the entire insertion portion 104 of the device 100. A person skilled in the art will appreciate that the second rotation joint $J_2$ can be formed at various other locations, including just proximal of the three-bar linkage 110, as previously shown in the embodiment of FIG. 1A.

Figure 5A:
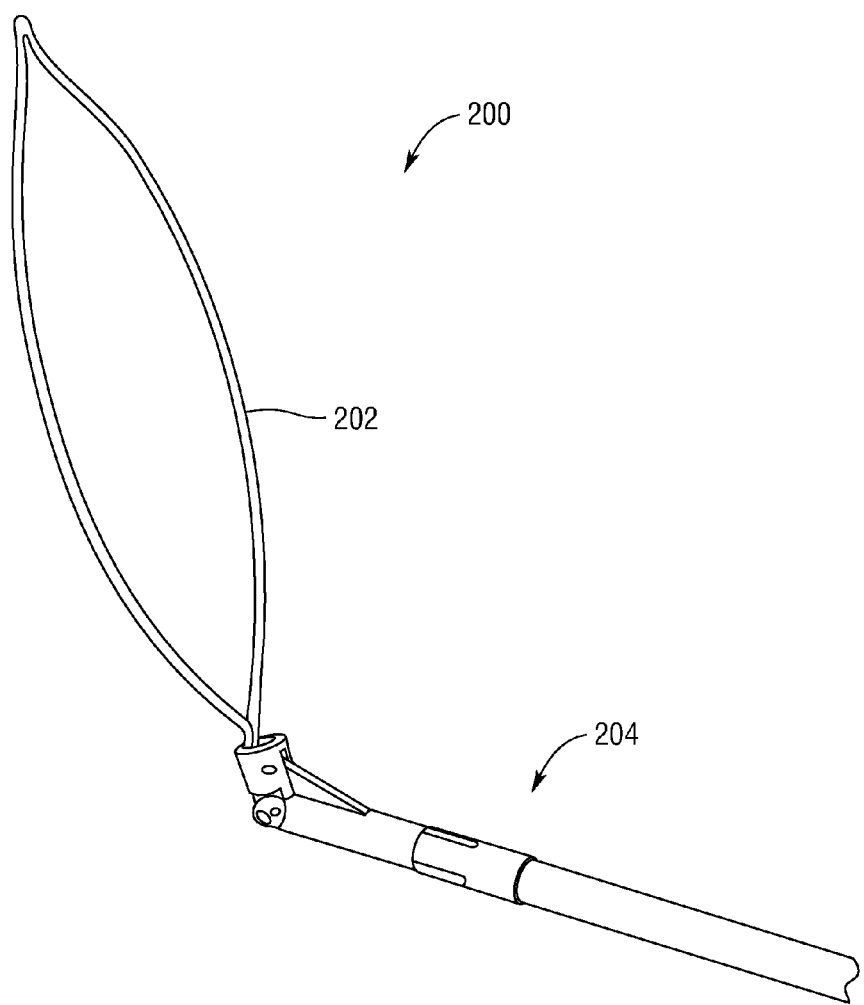
FIG. 5A is a perspective view of yet another embodiment of an insertion portion for use with a manually articulating device, showing an end effector with a snare loop.
Figure 5B:
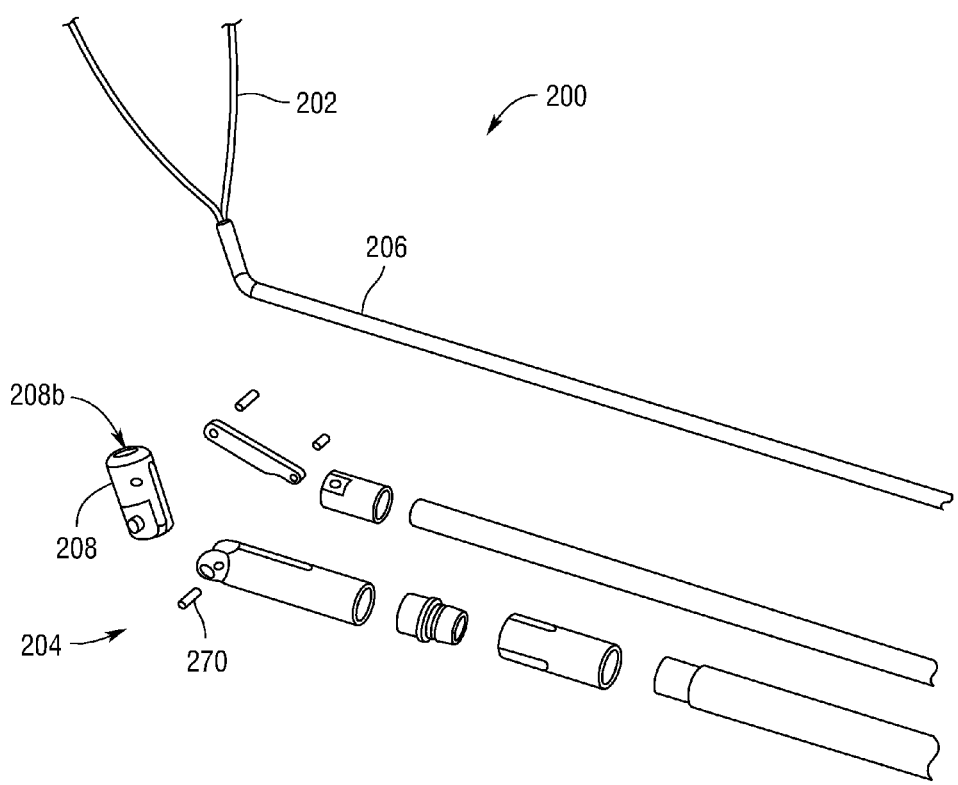
FIG. 5B is an exploded view of the insertion portion of FIG. 5A.

While devices discussed above are described and shown in connection with grasper jaws, a variety of other end effectors for performing various surgical procedures can be used. For example, as previously described with respect to FIGS. 2A-2B, the end effector 14' can be in the form of biopsy forceps. Other jaw types may be used, including scissors and other cutting devices. The end effector can also include other features, such as a tissue-penetrating spike 41' formed between the jaws 18a', 18b', as further shown in FIGS. 2A-2B. The illustrated spike 41' can be used in combination with any type of end effector having opposed jaws, or with various other end effectors known in the art. FIGS. 5A-5B illustrate another embodiment of an end effector in the form of a snare loop. As shown, the snare loop is formed from an elongate wire 200 that is folded such that a looped portion 202 of the wire 200 extends from a distal end 204$_b$ of the insertion shaft 204 of the device. The trailing ends of the wire 200 can extend through the device and form the actuation wire, or they can be coupled to an actuation wire, as previously described. As further shown in FIG. 5B, the wire 200 may be disposed within an insulating sheath 206 for insulating the device from any electrical energy delivered to the looped portion 202. The insulating sheath 206 can move in coordination with the wire 200, forming part of the actuation wire that is effective to actuate the end effector. The remaining components of the illustrated end effector are similar to those previously described with respect to FIGS. 1A-1D, except that the second link 208 can include a bore 208b formed in the distal end thereof for receiving the snare wire 200 and the insulating sheath 206 therethrough. In use, proximal movement of the snare wire 200 will pull the loop 202 proximally into the second link 208. As a result, the loop 202 will decrease in size, thus allowing the loop 202 to grasp and engage tissue to be removed. Conversely, distal movement of the snare wire 200 will push the loop 202 distally beyond the second link 208, thereby increasing a size of the loop 202. A decoupling member 270 (FIG. 5B) may be used to isolate the movement of snare wire 200 from the articulation of the snare wire 200.

Figure 6:
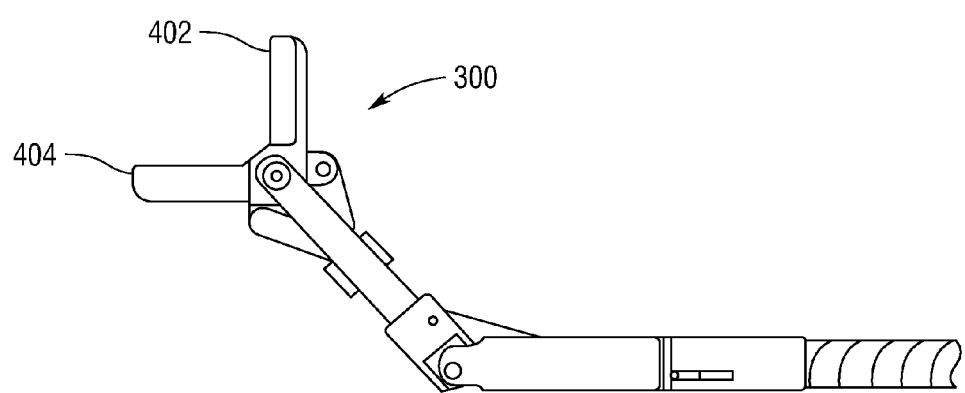
FIG. 6 is a perspective view of another embodiment of an end effector having scissors for use with a manually articulating device.

FIG. 6 illustrates another embodiment of an end effector that can be used with the manually articulating devices disclosed herein. A pair of scissors 300 has a configuration similar to the biopsy jaws and forceps previously described herein; however, each jaw 402, 404 has a blade-like configuration for cutting tissue. A decoupling member may be used to isolate the actuation of the scissors (i.e, the cutting action) from the articulation of the scissors. A person skilled in the art will appreciate that a variety of other end effectors can be used other than those described and illustrated herein.

As indicated above, the various devices disclosed herein for controlling movement of a working end of a surgical device can be used in a variety of surgical procedures, including endoscopic procedures, laparoscopic procedures, and in conventional open surgical procedures, including robotic-assisted surgery. In one endoscopic procedure, an elongate shaft of a surgical device, such as one previously disclosed herein, can be inserted through a natural orifice and a body lumen to position an end effector located at a distal end of the elongate shaft adjacent to tissue to be treated. An articulation actuator can be translated along a longitudinal axis of the elongate shaft to cause a three-bar linkage to laterally articulate the end effector in a direction substantially perpendicular to a longitudinal axis of the elongate shaft to allow the end effector to be angularly oriented relative to the elongate shaft. This can be achieved by actuating one or more actuation mechanisms formed on a handle of the device. The method may include rotating the end effector relative to the elongate shaft. In one embodiment, the three-bar linkage can rotate with the end effector relative to the elongate shaft. For example, the articulation actuator can be rotated relative to the elongate shaft to rotate both the three-bar linkage and the end effector. In another embodiment, the end effector can rotate relative to the three-bar linkage. Once the end effector is positioned as desired, the end effector can be used to perform a surgical procedure.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by the cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, and steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. A surgical device, comprising:
   a flexible elongate shaft defining a longitudinal axis between a proximal end and a distal end and dimensioned to fit in a working channel of an endoscope;
   a handle coupled to the proximal end of the flexible elongate shaft; and
   an articulation joint comprising
      a first end defining a first articulation axis and rotatably coupled to the distal end of the flexible elongate shaft,
      a second end defining a second articulation axis and coupled to an end effector, wherein the handle is configured to operatively couple to the end effector via an actuation wire extending along the flexible elongate shaft and the articulation joint,
      a pivot point pivotably coupling the first end and the second end, wherein the second end is pivotable relative to the first end about the pivot point between a straight position and an articulated position to angularly orient the first articulation axis relative to the second articulation axis, and
      a decoupling member positioned on the second end of the articulation joint and structured to divert the path of the actuation wire toward the pivot point when the second end is in the straight position and the articulated position to reduce a moment arm with respect to the pivot point when an actuation force is applied to the actuation wire, and wherein the actuation wire defines a first line proximal to the decoupling member and a second line distal to the decoupling member, and wherein the decoupling member geometrically constrains the actuation wire such that when the second end is in the straight position the first line and the second line together define a first non-zero angle and when the second link is in the articulated position the first line and the second line define a second non-zero angle;
   wherein the handle is adapted to selectively rotate the articulation joint and the end effector coupled thereto about the longitudinal axis, relative to the flexible elongate shaft.

2. The device of claim 1, wherein the second end is rotatably coupled to the end effector such that the handle is adapted to selectively rotate the end effector about the second articulating axis, relative to the first end.

3. The device of claim 1, wherein the actuation wire is adapted to translate along the longitudinal axis of the flexible elongate shaft to actuate the end effector, and wherein the actuation wire comprises a first segment proximal to the decoupling member and a second segment distal to the decoupling member, and wherein the second segment is aligned with the pivot point in the articulated position.

4. The device of claim 1, wherein the actuation wire is comprised of metal.

5. The device of claim 1, wherein the decoupling member is a pin.

6. The device of claim 5, wherein a lubricant coats at least a portion of the pin.

7. The device of claim 5, wherein the pin is rotatable in relation to the articulation joint.

8. The device of claim 1, wherein the decoupling member is unitary with the articulation joint.

9. A method of preparing an instrument for surgery, comprising:
   obtaining the device of claim 1;
   sterilizing the surgical device; and
   storing the surgical device in a sterile container.

10. A surgical device, comprising:
    a flexible elongate shaft comprising a proximal end and a distal end and dimensioned to fit in a working channel of an endoscope;
    an articulation joint comprising
       a first link defining a first articulation axis and coupled to the distal end of the flexible elongate shaft,
       a second link defining a second articulation axis and comprising a proximal end pivotally coupled to a distal end of the first link about a first pivot point and a distal end configured to couple to an end effector, wherein the second link is pivotable relative to the first link about the first pivot point between a straight position and an articulated position to angularly orient the second articulation axis relative to the first articulation axis, wherein the second articulation axis is configured to be substantially aligned with the first articulation axis when the second link is in the straight position and at an angle with respect to the first articulation axis when the second link is in the articulated position, and wherein the second link comprises a decoupling member;
       a third link having a distal end pivotally coupled to the second link about a second pivot point; and
    an actuation wire extending through the elongate shaft and the articulation joint, and operatively coupled to the end effector, wherein the actuation wire is translatable to actuate the end effector
       wherein the decoupling member is positioned on the second link and is configured to divert the path of the actuation wire toward the first pivot point when the second link is in the straight position and the articulated position to reduce a moment arm with respect to the first pivot point when an actuation force is applied to the actuation wire, wherein the actuation wire defines a first line proximal to the decoupling member and a second line distal to the decoupling member, and wherein the decoupling member geometrically constrains the actuation wire such that when the second link is in the straight position the first line and the second line together define a first non-zero angle and when the second link is in the articulated position the first line and the second line define a second non-zero angle.

11. The device of claim 10, comprising an articulation actuator extending through the flexible elongate shaft and having a distal end pivotally coupled to a proximal end of the third link about a third pivot point, wherein the articulation actuator is adapted to translate along the flexible elongate shaft such that the translation pivots the second link and the end effector relative to the first link and the flexible elongate shaft about the first pivot point.

12. The device of claim 10, wherein the decoupling member is fixably mated to the second link.

13. The device of claim 10, wherein the decoupling member is a pin.

14. The device of claim 13, wherein proximal movement of the articulation actuator is adapted to pivot the second link and the end effector from the straight position to the articulated position, and wherein distal movement of the articulation actuator is adapted to pivot the second link and the end effector from the articulated position to the straight position.

15. The device of claim 14, wherein the actuating wire is comprised of metal.

16. The device of claim 15, wherein the end effector is selected from the group consisting of a grasper, a biopsy probe, a snare loop, forceps, and scissors.

17. The device of claim 13, where a lubricant coats at least a portion of the pin.

18. The device of claim 13, wherein the pin is rotatable relative to the second link.

* * * * *